(12) United States Patent
Teeger et al.

(10) Patent No.: US 11,642,585 B2
(45) Date of Patent: May 9, 2023

(54) SYSTEMS AND METHODS FOR DYNAMIC AND ACCURATE PITCH DETECTION

(71) Applicant: Strikezone Technologies, LLC, Redmond, WA (US)

(72) Inventors: Wayne Teeger, Redmond, WA (US); Dayne Sampson, Sammamish, WA (US); Joshua Mason, Mercer Island, WA (US)

(73) Assignee: Strikezone Technologies, LLC, Redmond, WA (US)

( * ) Notice: Subject to any disclaimer, the term of this patent is extended or adjusted under 35 U.S.C. 154(b) by 265 days.

(21) Appl. No.: 17/121,481

(22) Filed: Dec. 14, 2020

(65) Prior Publication Data

US 2021/0093940 A1    Apr. 1, 2021

Related U.S. Application Data

(63) Continuation of application No. 16/589,302, filed on Oct. 1, 2019, now Pat. No. 10,894,198.

(51) Int. Cl.
*A63F 13/00* (2014.01)
*A63B 71/06* (2006.01)
*A63B 24/00* (2006.01)
*A63B 102/18* (2015.01)

(52) U.S. Cl.
CPC ...... *A63B 71/0605* (2013.01); *A63B 24/0021* (2013.01); *A63B 71/0622* (2013.01); *A63B 2024/0009* (2013.01); *A63B 2024/0034* (2013.01); *A63B 2071/0625* (2013.01); *A63B 2071/0694* (2013.01); *A63B 2102/18* (2015.10); *A63B 2220/805* (2013.01); *A63B 2220/808* (2013.01); *A63B 2225/50* (2013.01); *A63B 2225/74* (2020.08)

(58) Field of Classification Search
None
See application file for complete search history.

(56) References Cited

U.S. PATENT DOCUMENTS

| | | | | |
|---|---|---|---|---|
| 4,855,711 A | * | 8/1989 | Harrop | A63B 71/0605 340/665 |
| 6,702,292 B2 | * | 3/2004 | Takowsky | A63B 71/0605 463/53 |
| 7,270,616 B1 | * | 9/2007 | Snyder | A63B 71/0605 473/453 |
| 9,457,253 B1 | * | 10/2016 | Rodriguez | A63B 24/0087 |

(Continued)

*Primary Examiner* — Paul A D'Agostino
(74) *Attorney, Agent, or Firm* — Ansari Katiraei LLP; Arman Katiraei; Sadiq Ansari

(57) ABSTRACT

Provided is a device for pitch detection within user-defined zones. The device detects a first gesture at a first height based on first output from all or some sensors, and detects a second gesture at a second height based on second output from all or some sensors. The device sets a top and bottom of the user-defined zone based on the first height and the second height, and tracks a location of an object relative to the user-defined zone based on third output, from a subset of sensors, that is generated in response to the object moving over or under the subset of sensors. The device discards output generated from two or more sensors that are not adjacent, measurements from adjacent sensors that differ by more than a distance threshold, and/or output from adjacent sensors with timestamps that differ by more than a time threshold.

23 Claims, 19 Drawing Sheets

(56) References Cited

U.S. PATENT DOCUMENTS

| | | | | |
|---|---|---|---|---|
| 9,744,419 | B1* | 8/2017 | Rodriguez | A63B 69/0002 |
| 9,956,465 | B1* | 5/2018 | Rodriguez | A63B 69/3608 |
| 10,112,097 | B2* | 10/2018 | LoDuca | A63B 69/0075 |
| 10,894,198 | B1* | 1/2021 | Teeger | A63B 71/0605 |
| 2003/0054898 | A1* | 3/2003 | Otten | A63B 69/3614 |
| | | | | 473/219 |
| 2004/0014538 | A1* | 1/2004 | Bennett | A63B 71/0605 |
| | | | | 473/456 |
| 2004/0239915 | A1* | 12/2004 | Anderson | G01P 3/68 |
| | | | | 356/28 |
| 2005/0085321 | A1* | 4/2005 | Diveglio | A63B 69/0002 |
| | | | | 473/453 |
| 2006/0178236 | A1* | 8/2006 | Mosbey | A63B 69/0002 |
| | | | | 473/451 |
| 2007/0013652 | A1* | 1/2007 | Kim | A61B 3/113 |
| | | | | 345/156 |
| 2007/0072705 | A1* | 3/2007 | Ono | G06T 7/586 |
| | | | | 473/451 |
| 2008/0201100 | A1* | 8/2008 | Petrov | G01S 5/16 |
| | | | | 356/3 |
| 2008/0248901 | A1* | 10/2008 | Mosier | A63B 71/0669 |
| | | | | 473/454 |
| 2010/0210377 | A1* | 8/2010 | Lock | A63B 69/3658 |
| | | | | 473/409 |
| 2013/0099922 | A1* | 4/2013 | Lohbihler | G08B 13/184 |
| | | | | 340/539.17 |
| 2016/0296797 | A1* | 10/2016 | Rosen | A63B 63/00 |
| 2017/0054950 | A1* | 2/2017 | Yeo | G01S 13/88 |
| 2017/0080315 | A1* | 3/2017 | Anglin | G16H 20/30 |
| 2017/0157484 | A1* | 6/2017 | Altshuler | G09B 19/0038 |
| 2018/0093160 | A1* | 4/2018 | Alhadeff | A63B 71/023 |
| 2018/0361223 | A1* | 12/2018 | Cherryhomes | A63B 71/0622 |

* cited by examiner

US 11,642,585 B2

SYSTEMS AND METHODS FOR DYNAMIC AND ACCURATE PITCH DETECTION

CLAIM OF BENEFIT TO RELATED APPLICATIONS

This application is a continuation of U.S. nonprovisional application Ser. No. 16/589,302 entitled "Systems and Methods for Dynamic and Accurate Pitch Detection", filed Oct. 1, 2019. The contents of application Ser. No. 16/589, 302 are hereby incorporated by reference.

BACKGROUND

Baseball officiating is subjective by virtue of relying on human umpires to decide whether a pitch crossing over home plate is a ball or a strike. The width of the strike zone (e.g., area over home plate in which the pitch is considered a strike) is equal to the width of home plate (e.g., 17 inches), while the height of the strike zone differs for each batter. The height of the strike zone is defined to be between the knees and the midpoint between the batter's shoulders and the top of the batter's pants.

The subjectivity of adjudicating balls and strikes, and the need for a human umpire complicates training and gameplay. For example, without an umpire, catcher, batter, or other trained person present by or behind home plate, a pitcher does not receive the necessary feedback for determining if the pitches are correctly executed and thrown in desired locations. Moreover, even with a trained person present by or behind home plate, the subjectivity of adjudicating balls and strikes may offer the pitcher differing calls especially when pitching to batters of different heights with different strike zones. For example, one umpire may perceive a particular pitch and location to be a ball, whereas a different umpire may perceive that same particular pitch and location to be a strike.

DETAILED DESCRIPTION OF PREFERRED EMBODIMENTS

Figure 1:
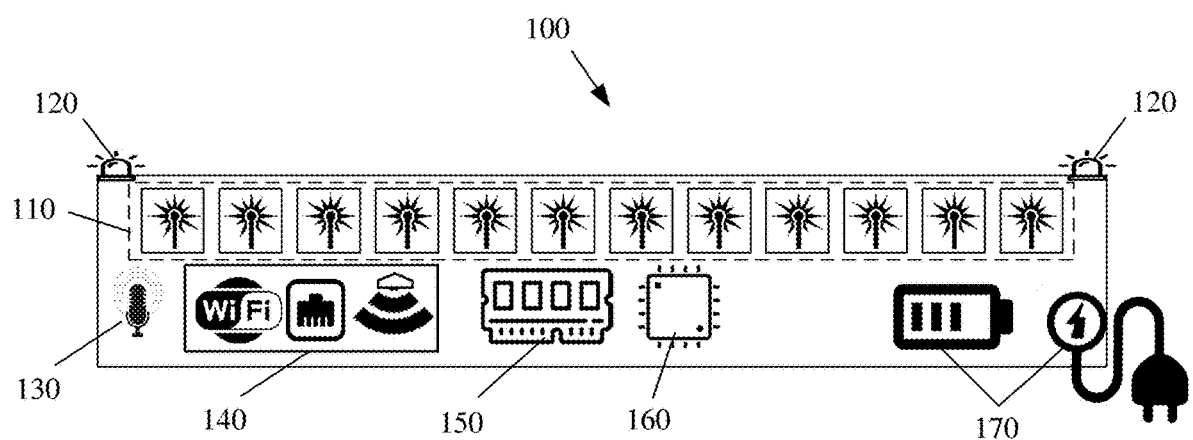
FIG. 1 illustrates example components of a tracking device in accordance with some embodiments presented herein.

The following detailed description refers to the accompanying drawings. The same reference numbers in different drawings may identify the same or similar elements.

Disclosed are systems and methods for dynamic and accurate pitch detection. The systems and methods can be used to enhance training, practice, and/or gameplay by providing consistent objective calls to a pitcher without input from a human. The systems and methods are primarily adapted for the game of baseball, but can be adapted for other uses that involve locating the position of a moving ball or object across a plane.

A tracking device is provided to implement some or all of the systems and methods for dynamic and accurate pitch detection. The tracking device may be placed at or by home plate, or the pitch tracking location where the position of the moving object is to be detected. The device may include a set of sensors that detect an x-y positioning of the moving object when the object moves past a location of the tracking device.

To differentiate from other devices that may detect or track positioning of a moving object, and to increase the accuracy of the tracking device relative to other devices, the systems and methods described herein include gesture configuration of the tracking device. The gestures include human interactions with the set of sensors prior to using the device for pitch detection. In some embodiments, the gestures can be used to configure the starting and ending height of the strike zone in order to adjust the strike zone for batters of different heights, thereby allowing the tracking device to adapt to different strike zones as would be experienced by a pitcher in actual gameplay rather than operate with a single static strike zone.

To further increase the accuracy of the tracking device, the tracking device may be implemented with methods for anomaly and/or false positive detection and removal. These methods allow the tracking device to differentiate between the target moving object and other objects (e.g., a bat, leaves, birds, foreign objects, body parts, dust, etc.). For instance, the tracking device may use the anomaly detection to determine that a first set of output produced by the set of sensors is from a swung bat, and may ignore the first set of output. The tracking device may use the anomaly detection to determine that a second set of output produced by the set of sensors corresponds to the target moving object (e.g., a thrown baseball) and meets all the requirements for a valid pitch, and therefore records or tracks the results derived from the second set of output.

In some embodiments, the anomaly detection may also increase the accuracy of a tracked pitch. For example, the tracking device may use the anomaly detection to determine which output from multiple triggered sensors of the device identifies the center point of the moving object. Consequently, the tracking device may be able to accurately locate the position of the moving object to within one quarter of an inch on the x-y plane where the moving object crossed over the tracking device. The result is an objectively accurate and consistent tracking of pitches within specific quadrants of a user-defined strike zone.

The tracking device may wirelessly integrate with other third-party devices to improve training, practice, and/or gameplay. In some embodiments, the tracking device or the system that includes the tracking device may receive or otherwise incorporate input from a third-party device that an umpire, catcher, pitcher, or other user may use to record their determination of a pitch being a ball or a strike and/or the placement of the pitch in or out of the strike zone. The pitch location determined by the sensors of the tracking device may be compared against the input from the third-party device in real-time to measure the accuracy and/or subjectivity of the user.

In some embodiments, the tracking device implements methods that create various games for training, practice, and/or gameplay purposes. For instance, the tracking device may include visual indicators or may use wireless messaging to instruct a pitcher to throw a specific sequence of pitches at different locations, and the set of sensors may track the accuracy of the pitcher in executing pitches that hit the different locations identified in the specific sequence of pitches.

FIG. 1 illustrates example components of tracking device 100 in accordance with some embodiments presented herein. Tracking device 100 may include sensors 110, visual indicators 120, microphone 130, network connectivity 140, memory or storage 150, processor 160, and power source 170. Tracking device 100 may include additional or fewer components in different embodiments. For instance, tracking device 100 may omit microphone 130 and may include a speaker to audibly identify detected pitches as balls or strikes, and/or to provide other instruction or notification to users. In some other embodiments, tracking device 100 may include additional visual indicators 120 so that there is one visual indicator 120 aligned with the position of each sensor 110, and/or include multiple rows of sensors 110 or more sensors 110 in a given row for more accurate or more granular object tracking.

In some embodiments, tracking device 100 has a width equal to or greater than a desired width across which device 100 tracks moving objects. In preferred embodiments, tracking device 100 has a width that is slight greater than the width of home plate in baseball. For instance, home plate may have a width of 17 inches, and tracking device 100 may have a width of 21 inches to extend 2 inches from either side of the home plate. One or more of sensors 110 may be placed on either side of the 2 inch extension beyond the width of home plate to detect and track balls to the right or left of the strike zone.

Tracking device 100 may have a low height (e.g., 6 inches) to not obstruct users when placed over the home plate. Additionally, the low height allows for tracking device 100 to be buried directly in front of the home plate or at the front edge of the home plate so that tracking device 100 (e.g., the top of tracking device 100) is flush to the ground or level with home plate.

In some embodiments, tracking device 100 may include 12 sensors 110 that are placed in a row and that are spaced 0.5 to 3 inches apart. In some other embodiments, tracking device 100 may include more or less sensors 110, and may reposition sensors 110 to be closer or further apart from one another. For instance, tracking device 100 may include multiple rows of sensors 110 to obtain additional measurements of the target moving object.

An individual sensor 110 is triggered and produces output when some physical object is detected directly above that sensor 110. The output of each sensor 110 may provide a height measurement and/or timestamp of when that sensor was triggered. The height measurement indicates the height of a moving object relative to the sensor 110 or some configured position. For instance, when tracking device 100 is placed into the ground so that sensors 110 are parallel to home plate, sensors 110 may output exact height measurements. However, when tracking device 100 is placed atop home plate with sensors 110 being 6 inches over the home plate, the height measurements output by sensors 110 may be adjusted to account for the 6 inches vertical displacement over home plate. In this case, the height measurements produced by sensors 110 may be increased by 6 inches to compensate for the 6 inch raised position of sensors 110 relative to home plate. In some embodiments, tracking device 100 may be suspended over the home plate (e.g., attached to the top of a batting cage) with sensors 110 pointing downwards towards the home plate. In some such embodiments, the height measurements output by sensors 110 may again be adjusted to account for the suspended and downward orientation of sensors 110 relative to the ground surface or the home plate. In any case, an application running on a mobile device or computer may be used to configure sensors 110 and/or bias the height measurements taken by sensors 110, if necessary, based on the placement or location of tracking device 100 relative to home plate or a ground surface.

Sensors 110 may include a set of lasers. The set of lasers may emit laser light, invisible light, or other light upward from the top of tracking device 100. Each sensor 110 can detect when an object crosses the light emitted from that sensor 110, and can obtain a height measurement for where the object intersects the light. For instance, the object may refract or reflect the light back to the sensor 110, and based on the angle of refraction or the timing of the reflection, the sensor 110 can measure the height of the object relative to the sensor 110.

In some embodiments, sensors 110 operate at a 400 microsecond ("μs") frequency. In some embodiments, sensors 110 may operate at a faster or slower frequency.

In addition to the height measurements, sensors 110 may also determine the speed of the moving object and/or the trajectory of the moving object. A baseball has a particular size and diameter. Accordingly, tracking device 100 may compute the speed of a baseball based on the frequency of sensors 110 and the time between the first detection of the baseball by one or more sensors 110 and the last detection of the baseball by the same one or more sensors 110.

In some embodiments, sensors 110 may include other optical or acoustic instruments for obtaining one or more measurements about a moving object. For instance, the sensors 110 may include cameras, infrared sensors, and/or depth sensors in addition to or instead of lasers.

Visual indicators 120 provide visual output to users. The visual output may provide feedback, instruction, and/or confirmation to users. Visual indicators 120 may flash different colors and/or may flash in difference sequences to generate the visual output.

In some embodiments, visual indicators 120 may use different colors and/or flashing sequences to indicate when tracking device 100 has entered a configuration mode, when a first end (e.g., top or bottom) of the strike zone has been set with a gesture or command, and when a second end of the strike zone has been set with a gesture or command. Visual indicators 120 may illuminate with different colors and/or flashing sequences to differentiate between balls and strikes, and may further illuminate with different colors and/or flashing sequences to indicate a strike zone quadrant where the pitch is detected (e.g., one flash of a first color to indicate a strike in the upper right quadrant, one flash of a second color to indicate a strike in the upper middle quadrant, one flash of a third color to indicate a strike in the upper left quadrant, two flashes of the first color to indicate a strike in middle right quadrant, etc.).

Visual indicators 120 may be used to instruct users on actions to take. For instance, visual indicators 120 may use different colors and/or flashing sequences to indicate a particular strike zone quadrant where a pitcher should throw a next pitch. Visual indicators 120 may also use the different colors and/or flashing sequences to specify a particular type of pitch (e.g., fastball, slider, breaking ball, change up, etc.) for the pitcher to throw.

Visual indicators 120 may include one or more light emitting diodes ("LEDs") or other lights that are visible when outdoors from a distance. In some embodiments, visual indicators 120 may include a distinct indicator for each sensor 110, or a distinct indicator for each quadrant of the strike zone. By activating a specific indicator corresponding to a specific sensor 110 or a specific quadrant, tracking device 100 may simplify the instruction on where a pitch is to be thrown or the feedback for where a pitch was detected. In some embodiments, visual indicators 120 may include a display that can present different symbols or characters.

In some embodiments, visual indicators 120 may include one or more lights that are located about the top tracking device 100, and that are used to convey information to a batter or umpire standing over tracking device 100. In some embodiments, visual indicators 120 may include one or more lights that are located on a front face of tracking device 100, and that are used to convey the same or different information to a pitcher that a distance away from tracking device 100.

Microphone 130 may be an optional component to support one or more methodologies implemented by tracking device 100. For instance, microphone 130 may record an audible call made by an umpire or nearby user after a pitch is detected using sensors 110. The input captured by microphone 130 may then be compared against the sensor output to determine if the audible call was correct or accurate. For instance, the spoken phrase "ball" captured by microphone 130 may be compared against output from a subset of sensors 110 that indicate a pitch within the strike zone, and tracking device 100 may determine that the audible call was incorrect based on the comparison of microphone 130 input and sensors 110 output.

Network connectivity 140 may include wired or wireless means of communicating with other devices and/or systems. Network connectivity 140 may include one or more Bluetooth, WIFI, Fourth Generation ("4G"), or Fifth Generation ("5G") network radios for wireless communications with other devices and/or systems.

Network connectivity 140 may be used to receive messaging for configuring tracking device 100. For instance, network connectivity 140 may receive messaging for calibrating the height of sensors 110 relative to the home plate or ground surface, or for selecting between different configured or stored user-defined strike zones.

Network connectivity 140 may also be used to transmit messaging. The transmitted messaging may include providing positioning of detected pitches to a user device so that the user can view the results and/or accuracy of the pitches on the user device. For instance, the transmitted messaging may present a strike zone quadrant on the user device and a location for each pitch of a sequence of pitches thrown by a pitcher to one or more batters. The messaging may provide additional information about each pitch (e.g., velocity, pitch type, etc.) or the batter (e.g., contact made, no swing, etc.).

The transmitted messaging may include providing a pitch plan to a user device, and the pitch plan may then be displayed on the user device in order to instruct the pitcher on what pitches to throw and where to locate each pitch.

Memory or storage 150 may store the instructions executed by processor 160. Memory or storage 150 may also store configuration information for different users including different strike zones that users custom-define using the supported gestures. Memory or storage 150 may also store pitch plans and tracked position information for different detected pitches and/or moving objects. The position information may include positional coordinates that are mapped against a selected strike zone. From the position information, additional information may be derived for each pitch, including whether the pitch was a ball or strike and/or the position of the pitch within or outside the strike zone quadrants. Other information including the pitch velocity, type of pitch, etc. may be stored and catalogued for different pitchers and/or batters in memory or storage 150.

Processor 160 may include an analog-to-digital converter for receiving and analyzing output from sensors 110. Processor 160 may include logic and/or circuitry for determining balls and strikes, for locating pitches within quadrants of a user-defined strike zone, and/or for tracking the accuracy of calls made by users using third-party devices or via input received from microphone 130. Processor 160 may also control activation of visual indicators 120 and/or communicate with other devices using network connectivity 140. In particular, processor 160 may signal a sequence of desired pitches or pitch locations and/or results of detected pitches via visual indicators 120 and/or network connectivity 140.

Power source 170 may include an onboard battery for powering operation of tracking device 100. Power source 170 may, alternatively or additionally, include wiring for connecting tracking device 100 to a continuous power supply (e.g., an outlet).

Figure 2:
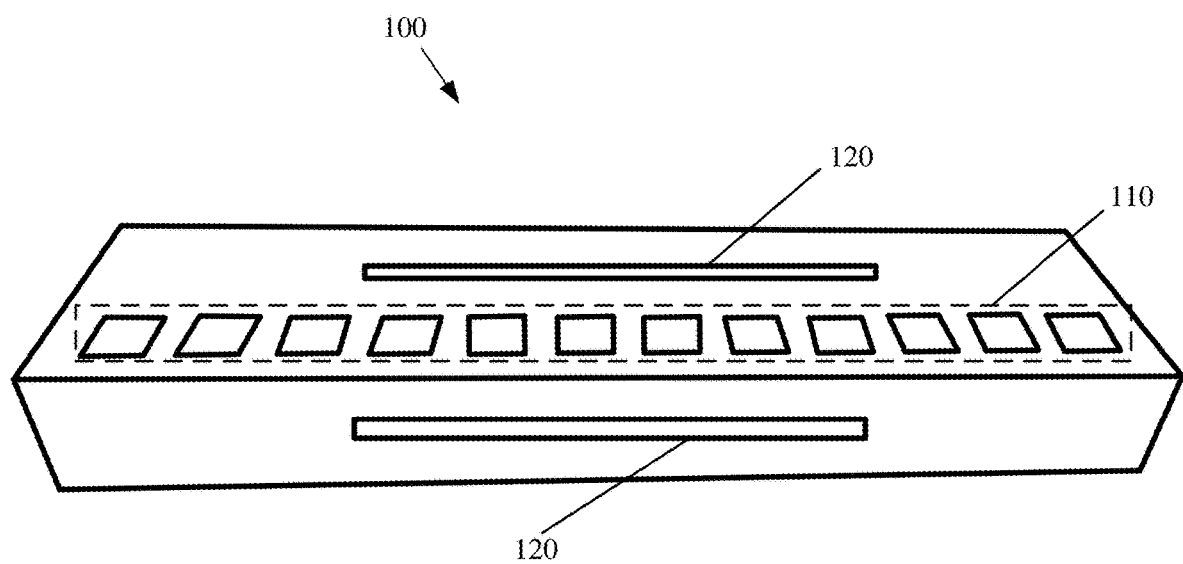
FIG. 2 provides an example external perspective view of the tracking device in accordance with some embodiments presented herein.

FIG. 2 provides an example external perspective view of tracking device 100 in accordance with some embodiments presented herein. As shown in FIG. 2, visual indicators 120 may include a first strip of lights about the front of device 100 and/or a second of lights about the top of device 100 that can illuminate with different colors and that can flash with different light sequences. Sensors 110 may be located towards the front or back of device 100 and closest to the edge of home plate or where measurements are to be taken.

Figure 3:
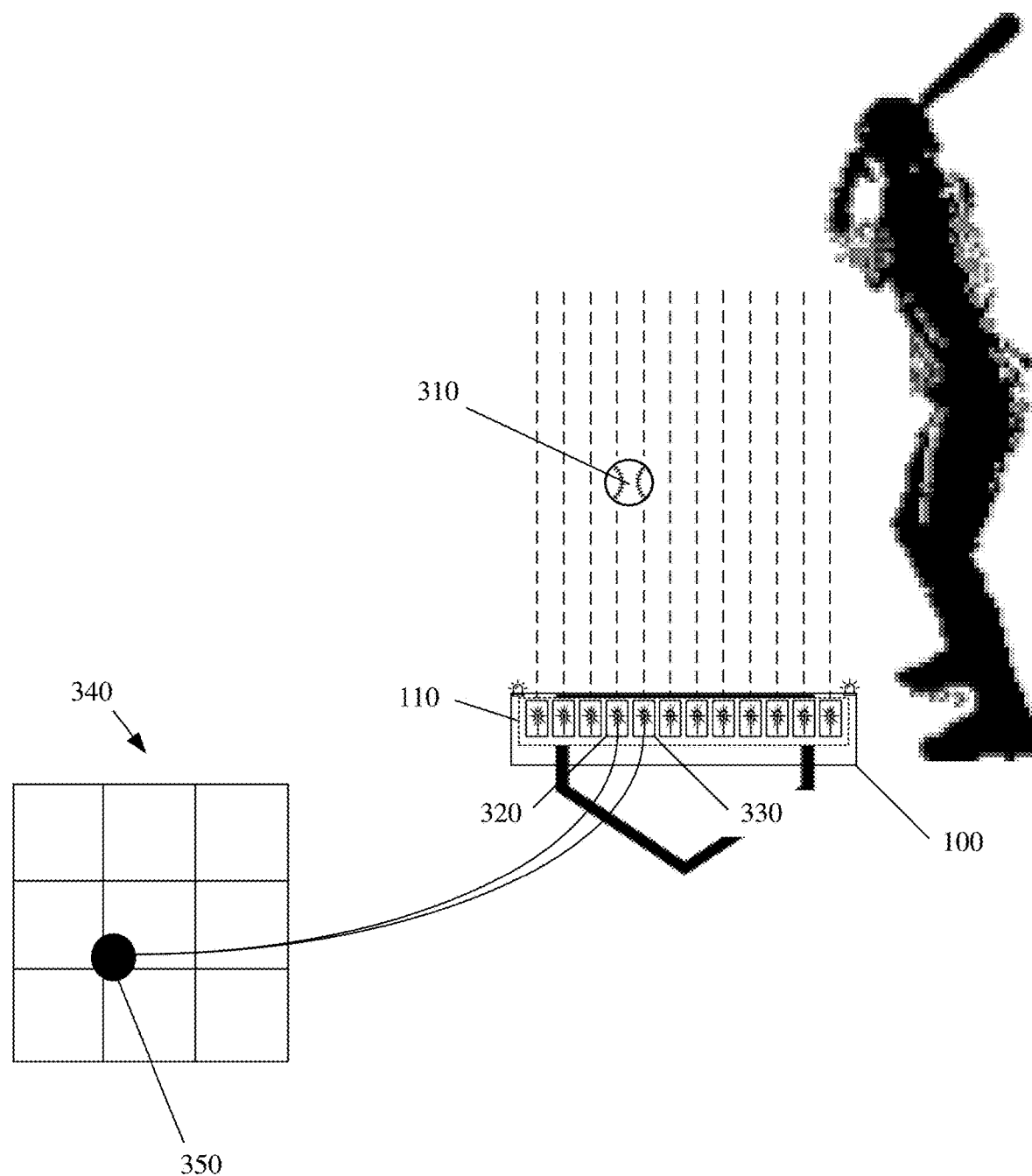
FIG. 3 illustrates example operation of the tracking device in accordance with some embodiments presented herein.

FIG. 3 illustrates example operation of tracking device 100 in accordance with some embodiments presented herein. FIG. 3 illustrates object 310 (e.g., a baseball) passing through lasers emitted from two adjacent sensors 320 and 330 from the set of sensors 110.

Sensors 320 and 330 obtain and output height measurements in response to being triggered by the passage of object 310 or in response to detecting object 310. Tracking device 100 can locate the horizontal position of object 310 in quadrants of strike zone 340 based on the positioning of sensors 320 and 330 in the set of sensors 110 and/or the positioning of sensors 320 and 330 on tracking device 100. Tracking device 100 can further locate the vertical position of object 310 in the quadrants of strike zone 340 based on the height measurements output from sensors 320 and 330.

As shown in FIG. 3, tracking device 100 may track position 350 in strike zone 340 based on the output from sensors 320 and 330, and tracking device 100 may determine that object 310 resulted in a strike call. Tracking device 100 may output the call result using visual indicators 120 or via messaging that is passed using network connectivity 140. Tracking device 100 may also output data providing position 350 in strike zone 340 using visual indicators 120 or via messaging that is passed using network connectivity 140.

In baseball, different batters are provided different strike zones that correspond to their height. Accordingly, a first batter that is 6 foot 5 inches tall and that has an erect batting stance will have a strike zone that is elevated and that is larger in height than a second batter that is 5 foot 8 inches tall and that has a crouched batting stance. Consequently, the same pitch may result in a strike for the first batter, and may result in a ball for the second batter. By rule, the strike zone in baseball should be between the knees and the midpoint between the batter's shoulders and the top of the batter's pants.

Tracking device 100 can adapt the strike zone, that it uses to differentiate between balls and strikes, for batters of different heights. The non-static and dynamic strike zones used by tracking device 100 increase the accuracy and effectiveness of tracking device 100 relative to other devices that use a fixed or static strike zone. By adapting the strike zone, tracking device 100 can account for factors that pitchers adjust to during live games and/or when facing different batters.

Tracking device 100 supports a set of gestures that users can input via sensors 110 to define a custom strike zone. Tracking device 100 may then use the custom strike zone to classify pitches as balls and strikes, and to locate the pitches within quadrants that are adapted based on the dimensions of the custom strike zone. In other words, tracking device 100 adjusts each quadrant according to the overall size of the user-defined strike zone. In some embodiments, tracking device 100 may compute 9 equal sized quadrants that are arranged in 3 rows for each user-defined strike zone. In some other embodiments, tracking device 100 may compute more or less quadrants that are of equal or different sizes for a user-defined strike zone in order to focus pitches in certain locations and/or increase or decrease the difficulty of hitting specific targets or locations within the user-defined strike zone.

Figure 4:
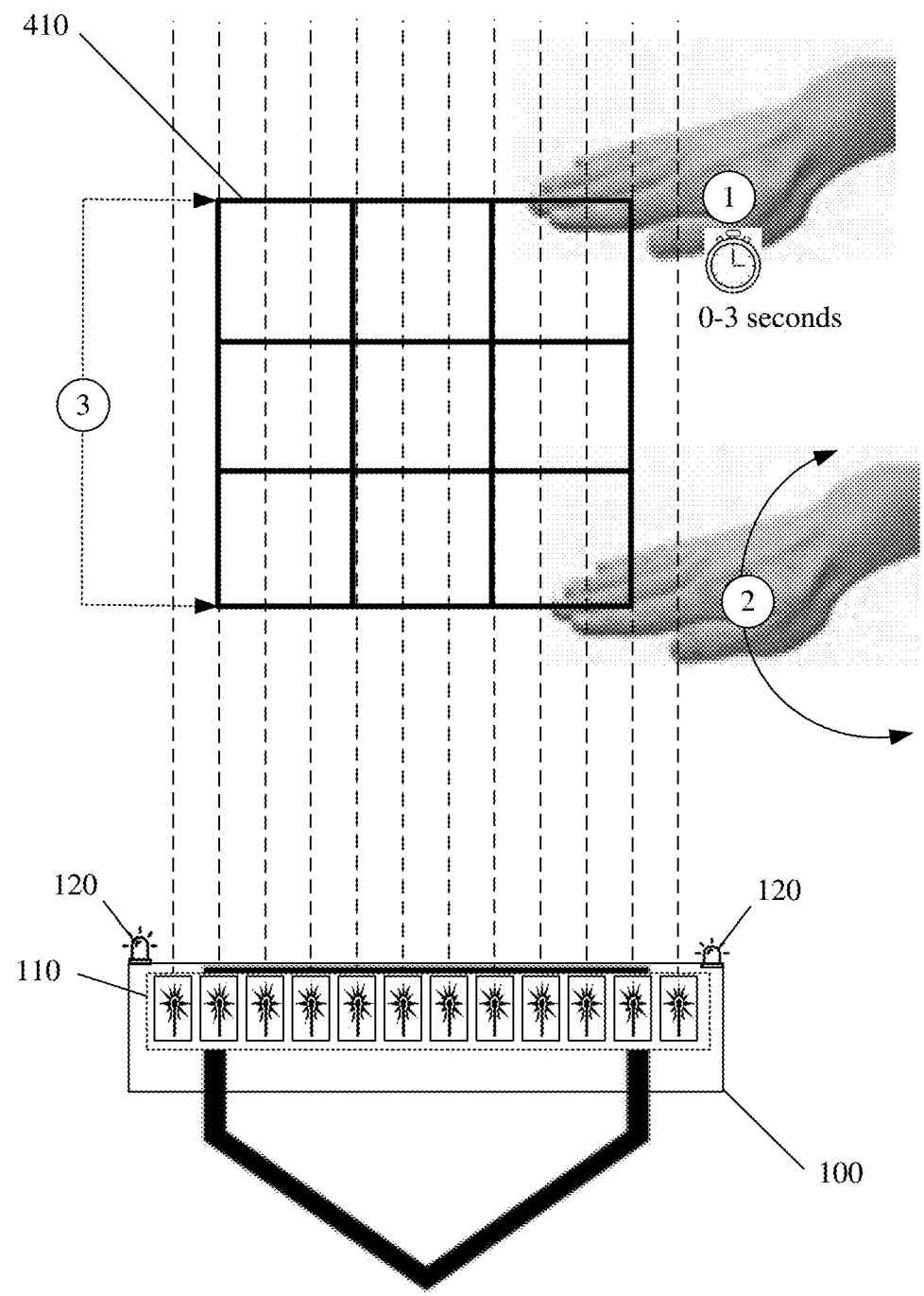
FIG. 4 illustrates an example set of gestures for configuring the tracking device with a user-defined strike zone in accordance with some embodiments presented herein.

FIG. 4 illustrates an example set of gestures for configuring tracking device 100 with a user-defined strike zone in accordance with some embodiments presented herein. As shown in FIG. 4, a user may place (at 1) a hand over some or all sensors 110 to set a first height for user-defined strike zone 410. In some embodiments, setting the first height may include performing a first gesture in which the user keeps his hand at the first height for a threshold amount of time. Keeping the hand at a fixed height for the threshold amount of time may cause tracking device 100 to enter a strike zone setting or configuration mode and to take a first measurement for the first height based on the detected height of the user's hand. For instance, the user may place (at 1) his hand over some or all sensors 110 for three seconds to activate the configuration mode and to set the first height. The first height may include the top or bottom of user-defined strike zone 410, wherein the determination of the top or bottom is subsequently determined based on whether a second height measurement, taken after the first height measurement, is above or below the first height measurement. In FIG. 4, the first height is used to set the top of user-defined strike zone 410 which should correspond to the midpoint between the user's shoulders and beltline.

In some embodiments, tracking device 100 may differentiate between a left-handed batter and a right-handed batter when configuring user-defined strike zone 410 based on which sensors 110 detect the user's hand. In FIG. 4, the rightmost sensors 110 detect the user's hand, and tracking device 100 may therefore configure user-defined strike zone 410 for a right-handed batter. The differentiation between a left-handed batter and a right-handed batter may be for determining which side of the strike zone is inside relative to the batter, and which side of the strike zone is outside relative to the batter. For instance, some pitchers may have difficulty pitching inside to a batter because of the presence of the batter's body. Accordingly, the differentiation of the strike zone for left-handed batters and right-handed batters can aide the user in reviewing pitch results and/or data at a subsequent time.

Tracking device 100 may provide visual confirmation once the first height is set. The visual confirmation may be provided by flashing or activating visual indicators 120.

After setting the first height for user-defined strike zone 410, the user may move his hand to set the second height of user-defined strike zone 410. The user may use a second gesture to indicate when the second height should be set. For instance, the user may wave (at 2) his hand to set the second height. A side-to-side waving of the hand may cause one or more sensors 110 to be repeatedly triggered, and the repeated triggering of sensors 110 may result in the second height being set.

The second height can be above or below the first height. Tracking device 100 automatically adjusts the top of user-defined strike zone 410 according to whichever of the first height and the second height is greater, and adjusts the bottom of user-defined strike zone 410 according to whichever of the first height and the second height is lower.

In response to detecting and setting the first and second heights, tracking device 100 may define coordinates or values for user-defined strike zone 410 that relative to coordinates or values for height measurements output by sensors 110. Tracking device 100 may also compute coordinates or values for different quadrants within user-defined strike zone 410 based on the coordinates or values for the first and second heights and the width of user-defined strike zone 410. Tracking device 100 may then use (at 3) user-defined strike zone 410 to determine balls and strikes for any subsequently detected moving objects, and to locate the position of those moving objects relative to user-defined strike zone 410. Additionally, tracking device 100 may enter (at 3) user-defined strike zone 410 into memory or storage 150 where it can be stored for subsequent selection and use.

In some embodiments, tracking device 100 may enter (at 3) user-defined strike zone 410 into memory or storage 150 with a unique user identifier. The unique user identifier may be obtained from a user device that is within wireless range of network connectivity 140. For instance, the user device may wirelessly communicate user credentials, a universally unique identifier ("UUID"), a telephone number, or other user identifier to tracking device 100 upon entering in wireless range of a wireless network created by tracking device 100. Tracking device 100 may then associate user-defined strike zone 410 with the user identifier so that the next time the user device with the user identifier is detected by tracking device 100, tracking device 100 may automatically define the strike zone for the user based on user-defined strike zone 410.

In some embodiments, the user may use an application to configure a name or identifier for user-defined strike zone 410, and tracking device 100 may receive and associate the name or identifier to user-defined strike zone 410. Accordingly, the user may subsequently use the application to select the name or identifier, and in response to a selection of the name or identifier, tracking device 100 may automatically configure the strike zone for the user based on user-defined strike zone 410.

Figure 5:
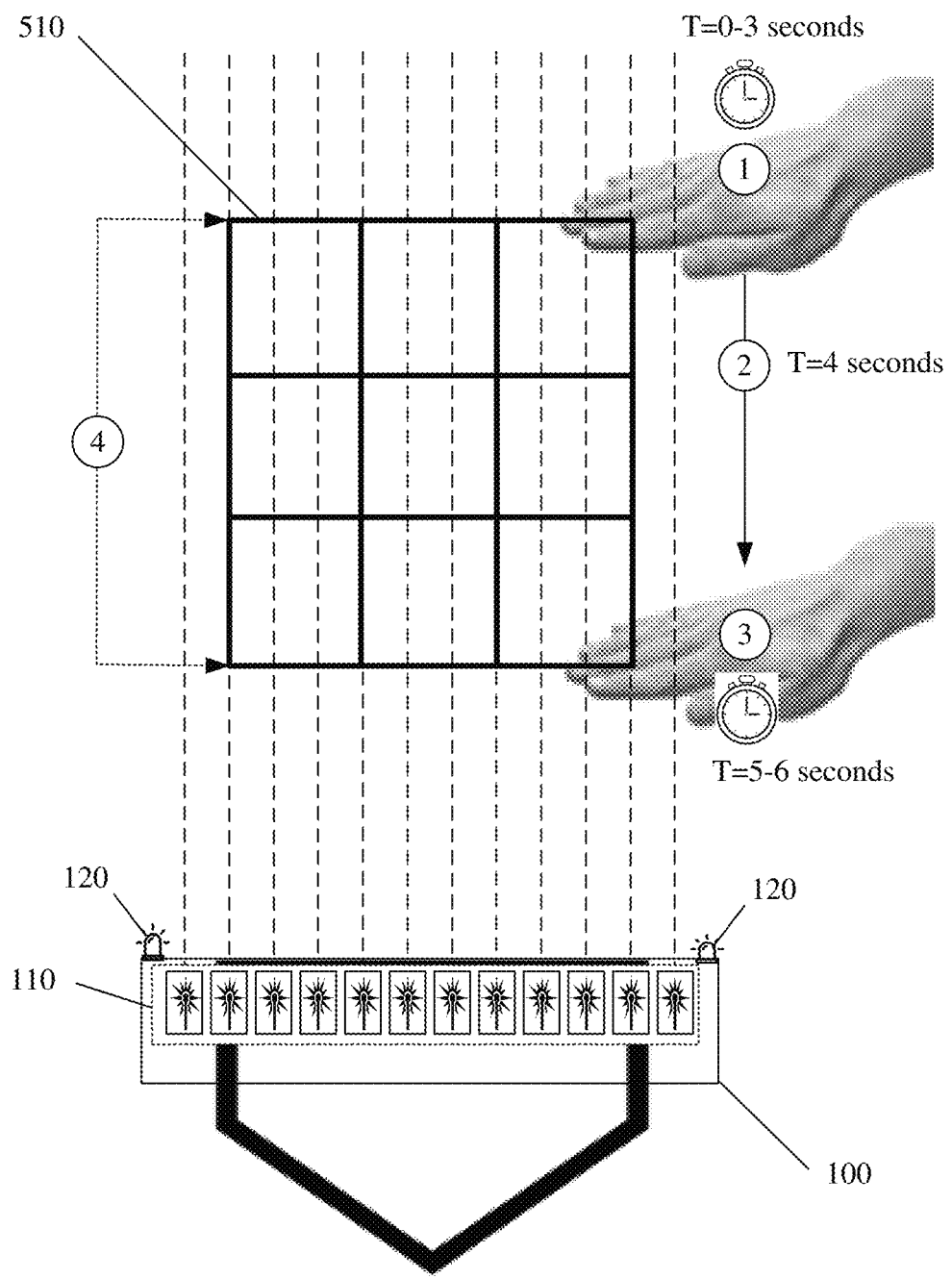
FIG. 5 illustrates an example of using the same gesture to configure a user-defined strike zone in accordance with some embodiments presented herein.

In some embodiments, the same gesture, instead of different gestures (e.g., holding and waving), may be used to set each of the first and second heights for user-defined strike zone 410. FIG. 5 illustrates an example of using the same gesture to configure user-defined strike zone 510 in accordance with some embodiments presented herein.

As shown in FIG. 5, the user may place (at 1) his hand over one or more sensors 110 at a first height, and may keep the hand at the first height for three seconds to initiate the configuration mode and to set the first height for either the top or bottom of user-defined strike zone 510. The user may raise or lower (at 2) his hand to a desired second height for an opposite end of user-defined strike zone 510. The user may keep (at 3) his hand over one or more sensors 110 at the second height for three seconds to set the second height for user-defined strike zone 510 and to exit from the configuration mode.

In FIG. 5, the same place and hold gesture is used to define the top and bottom of user-defined strike zone 510. The duration for the gesture may be greater or less than 3 seconds in different embodiments. In some embodiments, tracking device 100 may use visual indicators 120 to notify the user when the configuration mode has been initiated, when the first height is set, when the second height is set, and/or when the configuration mode is complete and user-defined strike zone 510 has been stored. Accordingly, the user need not guess on when to move his hand in order to set the different heights.

Figure 6:
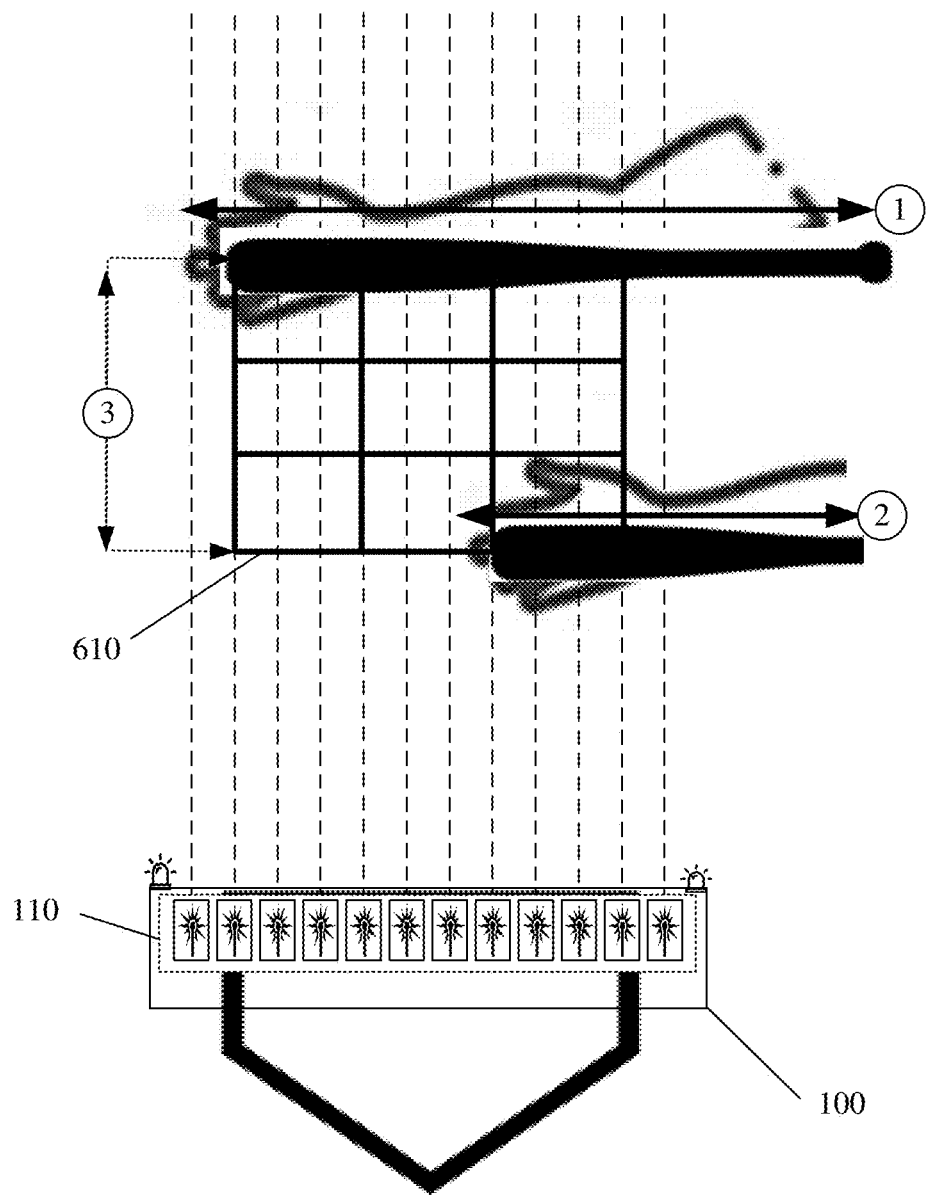
FIG. 6 illustrates an example of other gestures that may be used to configure the tracking device in accordance with some embodiments presented herein.

FIG. 6 illustrates an example of other gestures that may be used to configure tracking device 100 in accordance with some embodiments presented herein. In FIG. 6, the user may extend (at 1) his arm or a bat over all sensors 110 to set a first height for first end of user-defined strike zone 610. This first gesture may further include retracting the arm or bat to complete setting the first height. The user may then extend (at 2) his arm or the bat over a subset of sensors 110 (e.g., half of sensors 110) to set a second height for an opposite second end of user-defined strike zone 610. Tracking device 100 may receive input from sensors 110, process the input in order to detect the different gestures for configuring user-defined strike zone 610, and generate (at 3) user-defined strike zone 610 based on the first and second heights that are derived from user-provided inputs to sensors 110.

FIGS. 4-6 illustrate different gestures that can be detected by sensors 110 of tracking device 100, and that can be used to configure a user-defined strike zone with which tracking device 100 determines a result (e.g., ball or strike) and/or position (e.g., location on or around quadrants that are generated for the user-defined strike zone) of a detected moving object. Some embodiments recognize and use different gestures that than those described in FIGS. 4-6 to configure the user-defined strike zone. A gesture may include any user-performed action that can be detected by sensors 110 of tracking device 100.

In some embodiments, one or more of the gestures may be used to configure other parameters or aspects of tracking device 100. For instance, gestures may be used to change an operating mode of tracking device 100, including changing between different pitch plans, changing between different stored user-defined strike zones, changing operation of visual indicators 120 (e.g., turning on or off the lights), changing messaging feedback provided via network connectivity 140, placing tracking device 100 in a standby mode or waking tracking device 100 from the standby mode, etc.

Figure 7:
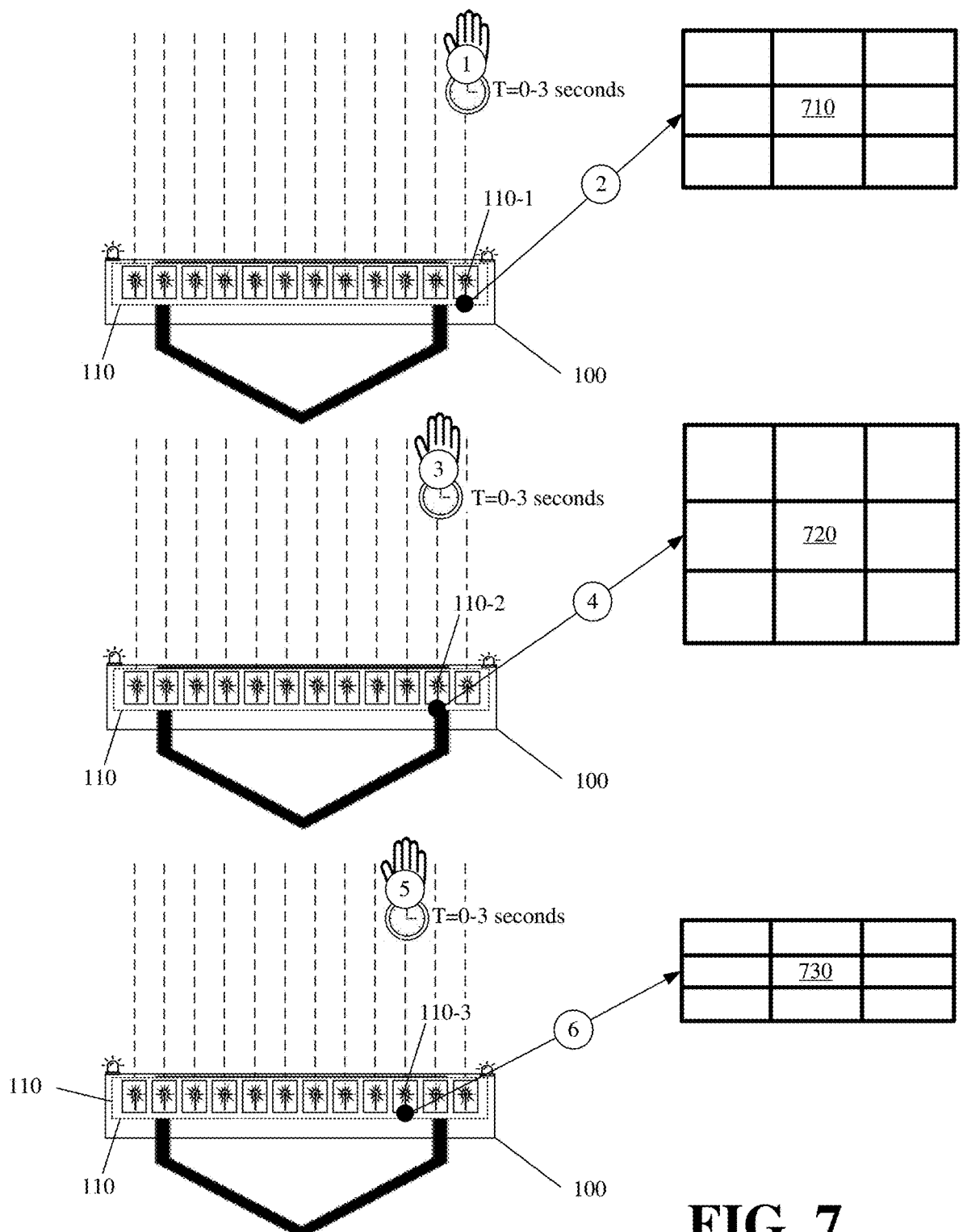
FIG. 7 illustrates an example of using gestures to select between different configured strike zones in accordance with some embodiments presented herein.

FIG. 7 illustrates an example of using gestures to select between different configured strike zones in accordance with some embodiments presented herein. As shown in FIG. 7, a user may perform (at 1) a particular gesture over first sensor 110-1 of the set of sensors 110 to configure (at 2) tracking device 100 with first strike zone 710, may perform (at 3) the particular gesture over second sensor 110-2 to configure (at 4) tracking device 100 with second strike zone 720, and may perform (at 5) the particular gesture over third sensor 110-3 to configure (at 6) tracking device 100 with third strike zone 730. The particular gesture may include holding a hand over one of sensors 110 for a threshold amount of time. In some embodiments, different gestures may be used to select between the different strike zones 710, 720, and 730.

Each of first strike zone 710, second strike zone 720, and third strike zone 730 may have different dimensions to accommodate users of different heights. For instance, first strike zone 710 may range from 16-36 inches above home plate, whereas second strike zone 720 may range from 14-40 inches above home plate. Each of first strike zone 710, second strike zone 720, and third strike zone 730 may be user-defined by the same user or different users and associated with the different sensors 110-1, 110-2, and 110-3 when defined. Each of first strike zone 710, second strike zone 720, and third strike zone 730 may be configured on tracking device 100 via an application that is running on a user device (e.g., a smartphone), and may be associated with a different sensor using the application.

In some embodiments, tracking device 100 may store a different strike zone for each of sensors 110, and/or store a different strike zone when performing the particular gesture over different numbers of sensors. For instance, tracking device 100 may select and configure a fourth strike zone in response to detecting the particular gesture over first and second sensors 110-1 and 110-2, and may select and configure a fifth strike zone in response to detecting the particular gesture over first, second, and third sensors 110-1, 110-2, and 110-3.

Figure 8:
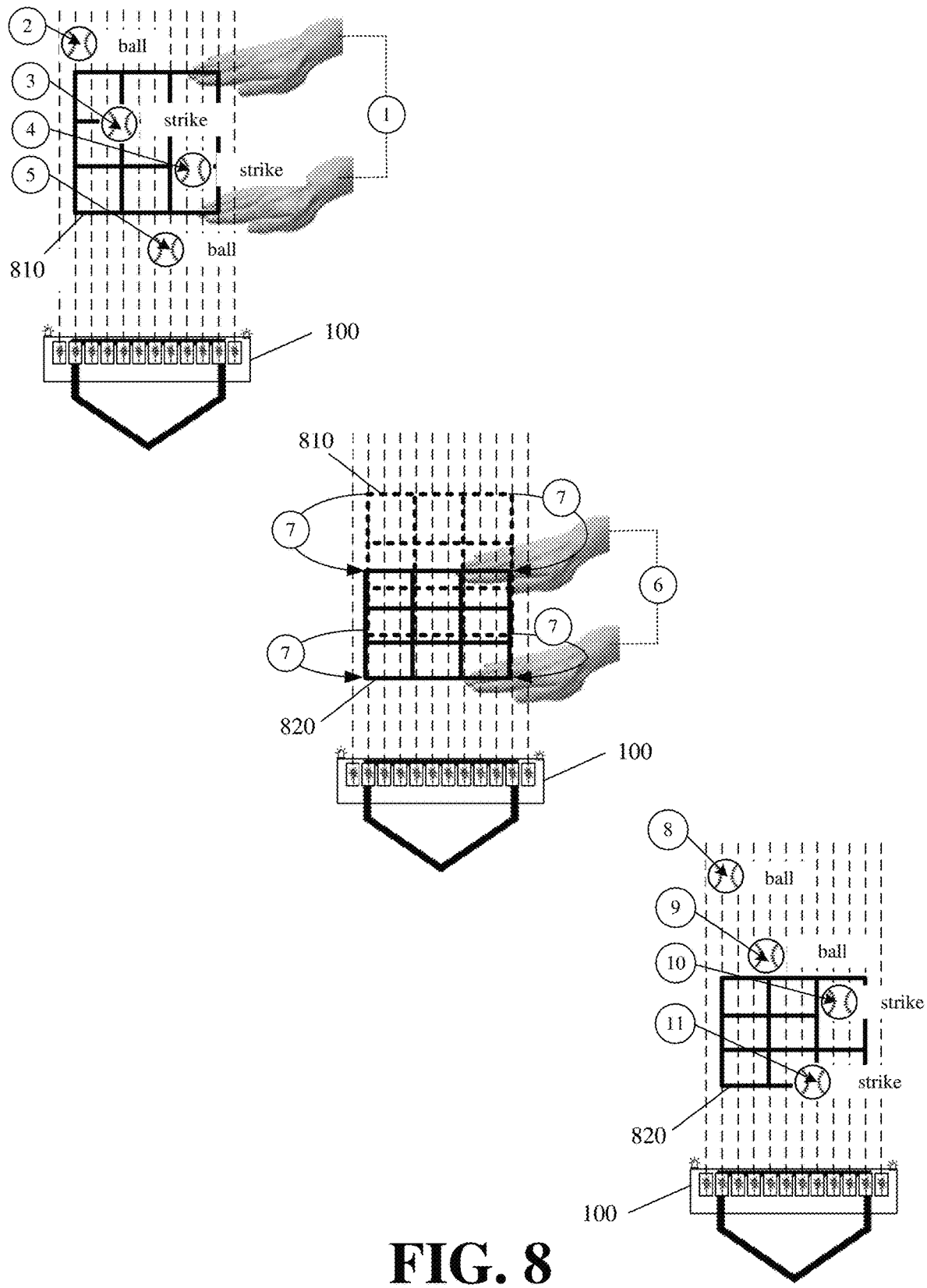
FIG. 8 illustrates an example of adapting the tracking device for different users in accordance with some embodiments presented herein.

FIG. 8 illustrates an example of adapting tracking device 100 for different users in accordance with some embodiments presented herein. A first user or batter may use a first set of gestures to configure (at 1) first user-defined strike zone 810. The first user or batter may be of a first height, and may therefore configure (at 1) first user-defined strike zone 810 according to the first height.

Tracking device 100 may track (at 2, 3, 4, and 5) a first sequence of pitches relative to first user-defined strike zone 810. In particular, the first sequence of pitches results (at 2) in a first pitch being classified as a ball as a result of the first pitch being tracked above first user-defined strike zone 810, results (at 3) in a second pitch being classified as a strike as a result of the second pitch being tracked within the left quadrants of first user-defined strike zone 810, results (at 4) in a third pitch being classified as a strike as a result of the third pitch being tracked in the right quadrants of first user-defined strike zone 810, and results (at 5) in a fourth pitch being classified as a ball as a result of the fourth pitch being tracked below first user-defined strike zone 810.

FIG. 8 then illustrates a second set of gestures that change (at 6) from first user-defined strike zone 810 to second user-defined strike zone 820. Second user-defined strike zone 820 may be smaller (e.g., have less distance between the top end and the bottom end) than first user-defined strike zone 810, and may have a bottom end that is lower than the bottom end of first user-defined strike zone 810 (e.g., a lower starting elevation). For instance, a second user or batter may be shorter than the first user or batter, and may configure second user-defined strike zone 820 to account for this difference in user height. Tracking device 100 may automatically resize (at 7) the quadrants of second user-defined strike zone 820 to fit within the top and bottom ends of second user-defined strike zone 820.

Tracking device 100 may track (at 8, 9, 10, and 11) a second sequence of pitches that are thrown in the same positions as the first sequence of pitches. However, tracking device 100 may track (at 8, 9, 10, and 11) the second sequence of pitches relative to newly configured and/or selected second user-defined strike zone 820 instead of previously configured and/or selected first user-defined strike zone 810. Second user-defined strike zone 820, because of its different dimensions and placement, causes the second sequence of pitches to be classified differently than the first sequence of the pitches even though the pitches of the two sequences are thrown in the exact same locations. Specifically, the second sequence of pitches results (at 8) in a fifth pitch, that is similar to the first pitch from the first sequence of pitches, being classified as a ball as a result of the fifth pitch being tracked above second user-defined strike zone 820, results (at 9) in a sixth pitch, that is similar to the second pitch, being classified as a ball as a result of the sixth pitch being tracked above second user-defined strike zone 820, results (at 10) in a seventh pitch, that is similar to the third pitch, being classified as a strike as a result of the seventh pitch being tracked in the right quadrants of second user-defined strike zone 820, and results (at 11) in an eighth pitch, that is similar to the fourth pitch, being classified as a strike as a result of the eighth pitch being tracked in the bottom quadrants of second user-defined strike zone 820. Consequently, first user-defined strike zone 810 and second user-defined strike zone 820 produce different outcomes and charting of pitches (e.g., location of pitches in strike zone quadrants) for the same sequence of pitches.

Figure 9:
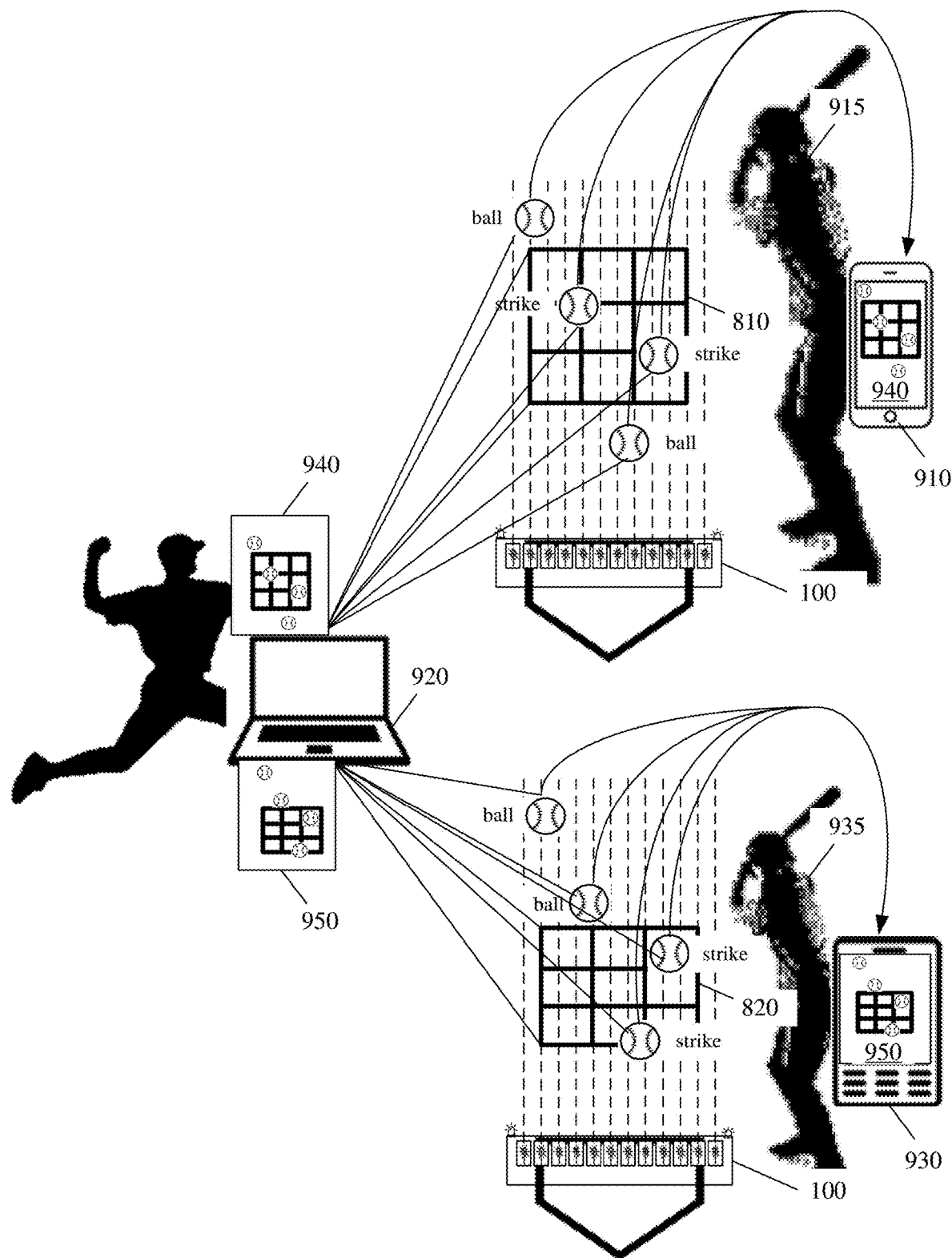
FIG. 9 illustrates output examples from the tracking device in accordance with some embodiments.

FIG. 9 illustrates output examples from tracking device 100 in accordance with some embodiments. Tracking device 100 may provide the output after each tracked pitch or after a sequence of tracked pitches. Tracking device 100 may provide the output via visual indicators 120, and also via wireless messaging that is passed to connected user devices 910, 920, and 930 as shown in FIG. 9. The output provided in FIG. 9 is based on the first and second sequences of pitches illustrated in FIG. 8.

User device 910 may be associated with first user or batter 915, and may connect to tracking device 100 when first user or batter 915 is near tracking device 100. For instance, tracking device 100 may use a Bluetooth radio to detect a user device that is within 10 feet of tracking device 100. User device 910 may be in the pocket of first user or batter 915, or may be placed next to tracking device 100 prior to the first sequence of pitches being thrown.

User device 920 may include a device of the pitcher, a coach, or other user. User device 920 may connect to tracking device 100 via Bluetooth, WIFI, or another wireless network technology. User device 920 may be identified with different parameters or privileges than user device 910. For instance, user device 920 may identify a user device of the pitcher, coach, or other user that receives all pitch information, whereas user device 910 may identify first batter or user 915 that receives only the pitch information for the first sequence of pitches when first batter or user 915 is in the batter's box and/or user device 910 is connected to tracking device 100.

The first sequence of pitches is classified and tracked according to first user-defined strike zone 810, and tracking device 100 may provide the output for the first sequence of pitches to user devices 910 and 920. In particular, user devices 910 and 920 may receive the calls (e.g., ball or strike) for each pitch of the first sequence of pitches as determined using first user-defined strike zone 810. Each pitch may be timestamped, identified in the sequence, and/or provided with additional identifying information (e.g., speed, pitch type, etc.). Additionally, tracking device 100 may provide user devices 910 and 920 with data for producing first visual representation 940 that tracks the first sequence of pitches in first user-defined strike zone 810.

In response to configuration of second user-defined strike zone 820 or in response to detecting user device 910 moving out-of-range of and/or disconnecting from tracking device 100, and user device 930 moving into range of and/or connecting to tracking device 100 before the second sequence of pitches, tracking device 100 may determine that second user or batter 935 has entered into the batter's box and is ready to receive the second sequence of pitches. Accordingly, tracking device 100 may alter the devices that receive subsequent output. In particular, output resulting from the second sequence of pitches is now provided to user devices 920 and 930, and may exclude user device 910 of first user or batter 915. In particular, user devices 920 and 930 may receive the calls (e.g., ball or strike) for each pitch of the second sequence of pitches as determined using second user-defined strike zone 820. Additionally, tracking device 100 may provide user devices 920 and 930 with data for producing second visual representation 950 that tracks the second sequence of pitches in second user-defined strike zone 820.

The data may be transmitted to each of user devices 910, 920, and 930 via network connectivity 140. Moreover, the data may be transmitted without any action by the users. For instance, user devices 910 and 930 may receive data for tracked pitches while user devices 910 and 930 are in range (e.g., a short distance) of tracking device 100, and tracking device 100 may automatically adjust the data according to whichever user-defined strike zone (e.g., user-defined strike zones 810 and 820) is configured or selected at the time different pitches are detected.

In this manner, tracking device 100 provides data that is relevant to each of devices 910, 920, and 930. For instance, each batter 915 and 935 may receive pitch information and/or data about the sequence of pitches faced by that batter 915 and 935, while a particular pitcher, coach, or other user can receive pitch information and/or data about all pitches through by that particular pitcher and/or other pitchers.

Figure 10:
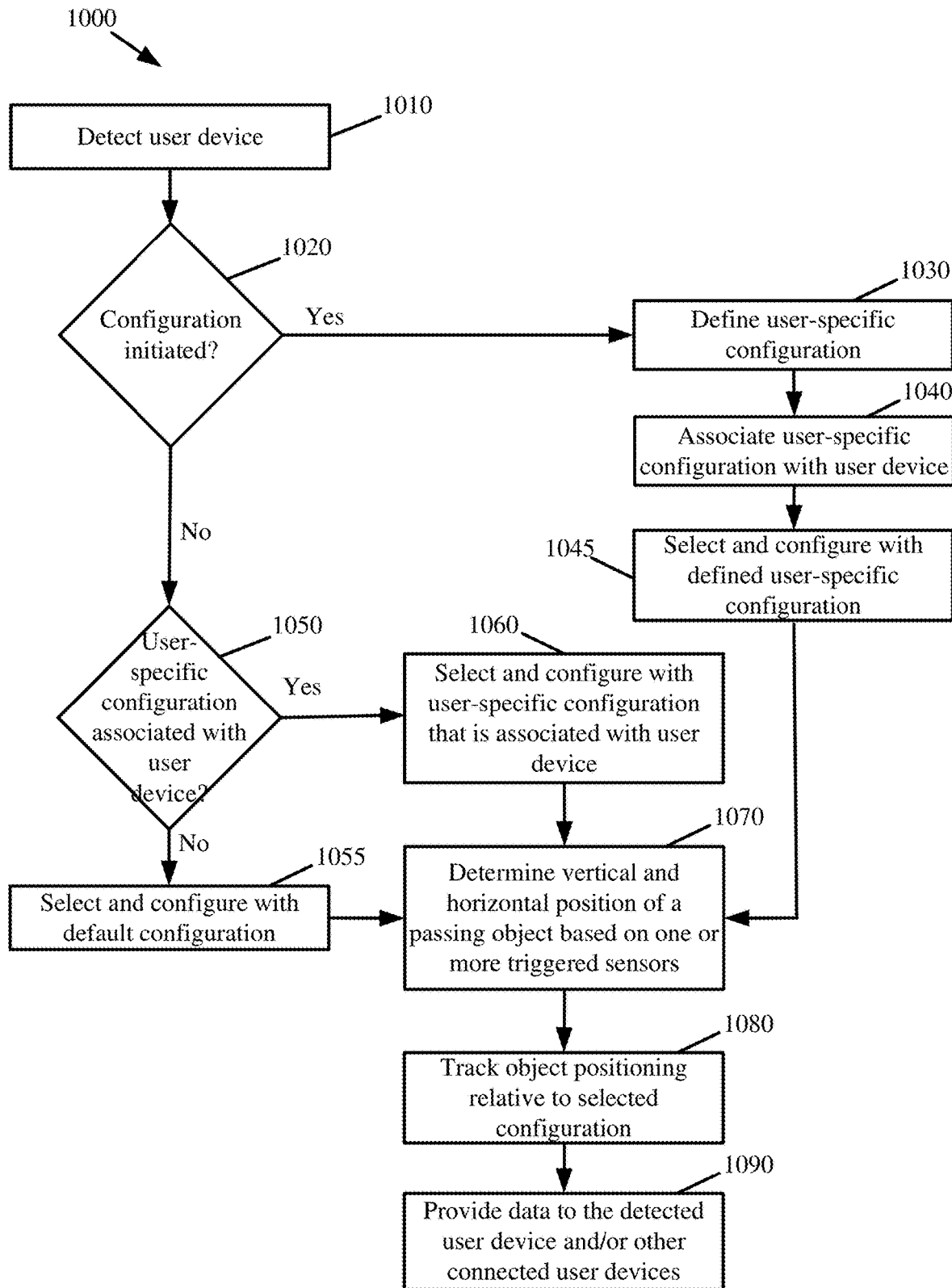
FIG. 10 presents a process for operation of the tracking device in accordance with some embodiments presented herein.

FIG. 10 presents a process 1000 for operation of tracking device 100 in accordance with some embodiments presented herein. Process 1000 may include detecting (at 1010) a user device. Detecting a user device may include detecting when the user device enters in range of a wireless network created by tracking device 100, connects to tracking device 100, and/or communicates with tracking device 100. The user device may include a smartphone, laptop, tablet, or any other network-enabled device that can connect to tracking device 100 via wired or wireless means.

Process 1000 may include determining (at 1020) if a configuration procedure is initiated. The configuration procedure may be initiated in response to tracking device 100 detecting, via sensors 110, one or more gestures that are performed by a user, wherein the one or more gestures are configured to initiate the configuration procedure. The configuration procedure may also be initiated in response to wireless messaging transmitted by the detected user device to tracking device 100. For instance, the user device may run an application with which a user can configure various parameters or aspects of tracking device 100. The configuration procedure may include a procedure for configuring a user-defined strike zone.

In response to determining (at 1020—Yes) that the configuration procedure is initiated, process 1000 may include defining (at 1030) a user-specific configuration based on received user input (e.g., gestures). The user-specific configuration may include a user-defined strike zone and/or other configurable parameters or aspects of tracking device 100. Process 1000 may include associating (at 1040) the user-specific configuration to the detected user device or a user of the detected user device. The association links the user-specific configuration to the user device so that the user-specific configuration can be defined once and reused, if desired, whenever a user with the user device returns to use tracking device 100. In some embodiments, the user-specific configuration may be stored with an identifier that uniquely identifies the user device or the associated user, and the identifier may be obtained by tracking device 100 upon connecting to or communicating with the user device. In some embodiments, tracking device 100 may store multiple user-specific configurations for the same user device, and a user may select between the stored user-specific configurations using an application that is running on the user device and that communicates with tracking device 100. Process 1000 may include selecting (at 1045) and configuring tracking device 100 with the defined user-specific configuration.

In response to determining (at 1020—No) that the configuration procedure has not been initiated, process 1000 may include determining (at 1050) whether a user-specific configuration is associated with the detected user device. Here, process 1000 involves selecting a user-specific configuration that was previously defined by the user of the user device if such a user-specific configuration exists so that the user does not have to redefine the configuration each time before using tracking device 100. For instance, the first time a user uses tracking device 100, the user may define a user-specified strike zone using the gestures. Tracking device 100 may associate that user-specified strike zone with an identifier that identifies the user or user device such that the next time the user returns to use tracking device 100, tracking device 100 can automatically select and configure with the previous user-specified strike zone.

In response to determining (at 1050—No) that a user-specific configuration is not associated with the user device (or the user of the user device), process 1000 may include selecting (at 1055) a default configuration and configuring tracking device 100 with the default configuration. The default configuration may include a default strike zone that is defined for an average batter, or may include a last configured user-defined strike zone (e.g., a configuration that may have been defined by another user).

In response to determining (at 1050—Yes) that a user-specific configuration is associated with the user device (or the user of the user device), process 1000 may include selecting (at 1060) that user-specific configuration from memory or storage 150, and configuring tracking device 100 with the selected (at 1060) user-specific configuration. In this scenario, tracking device 100 automatically retrieves and configures with a configuration that was previously specified by the user without the user having to redefine the configuration.

Regardless of the configuration that is selected (at 1045, 1055, or 1060), process 1000 may include determining (at 1070) a vertical and horizontal position of an object passing over tracking device 100 based on one or more triggered sensors 110 of tracking device 100. Process 1000 may include tracking (at 1080) the object positioning relative to the selected configuration (e.g., selected strike zone), and providing (at 1090) data relating to the object positioning to the user device and/or other connected user devices.

Sensors 110 may accurately determine the horizontal position of a moving object based on the location of one or more sensors 110 that detect the moving object. Sensors 110 may accurately determine the vertical position of a moving object based on measurements obtained from output of the triggered sensors 110 or sensors 110 detecting the moving object. However, objects other than a target object (e.g., a thrown ball) may produce output on one or more of sensors 110 leading to false positives and data inaccuracy. For instance, flies, birds, baseball bats, body parts, and/or other objects may create undesired output on one or more sensors 110, and that output can pollute the tracking data generated by tracking device 100.

Some embodiments implement and provide tracking device 100 with methods for anomaly detection and false positive removal. The anomaly detection differentiates between sensor measurements produced by a desired target object and sensor measurements produced by other undesired objects. Moreover, the anomaly detection ignores or removes the sensor measurements produced by the other undesired objects so that the results provided by tracking device 100 are accurate and do not contain data that must be manually filtered. The anomaly detection prevents tracking device 100 from tracking and recording anything and everything that is detected by sensors 110.

Figure 11:
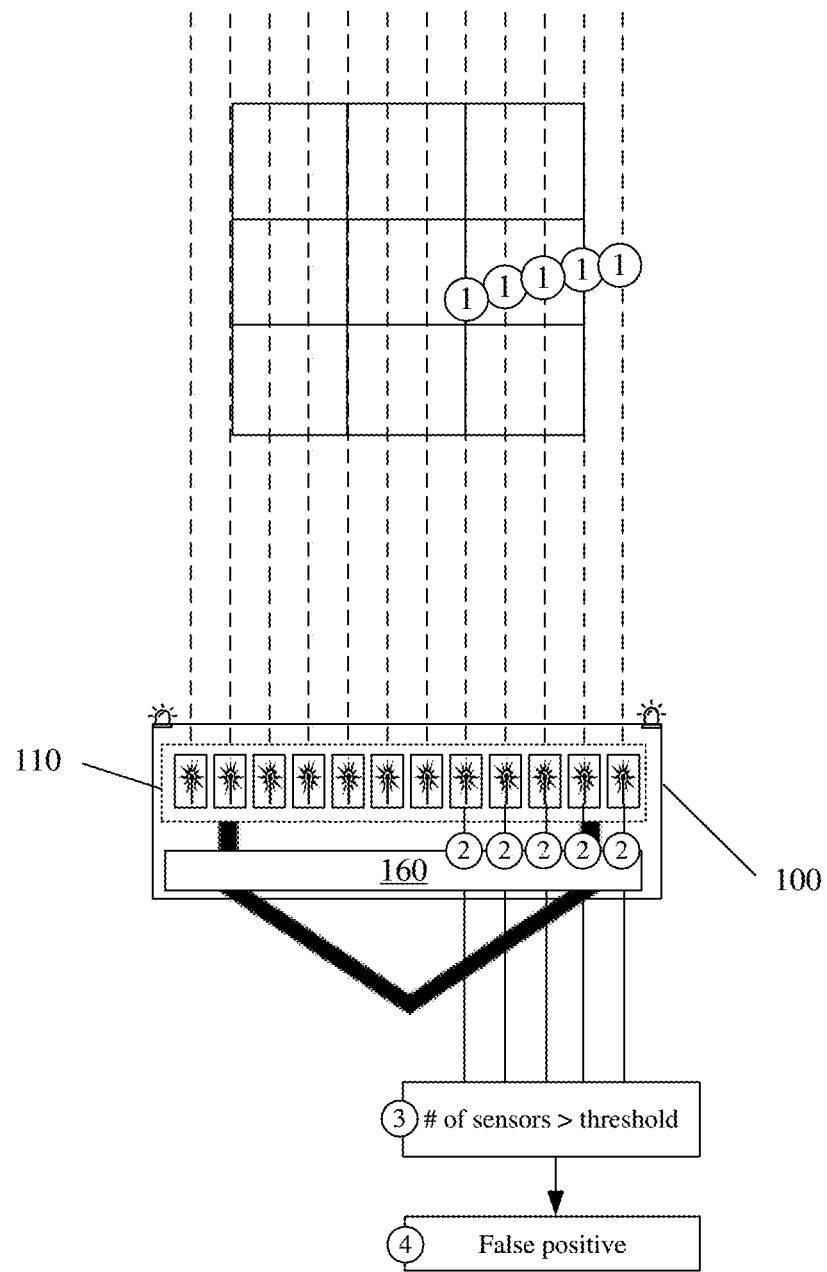
FIG. 11 illustrates an anomaly detection example that is based on the number of triggered sensors in accordance with some embodiments presented herein.

FIG. 11 illustrates an anomaly detection example that is based on the number of triggered sensors 110 in accordance with some embodiments presented herein. The anomaly detection illustrated in FIG. 11 may be directly implemented on tracking device 100 and/or by processor 160 when processing output from sensors 110. As shown in FIG. 11, a moving object simultaneously or contemporaneously (e.g., within a few milliseconds) produces (at 1) similar height measurements on 5 of 12 adjacent sensors 110.

Processor 160 may receive (at 2) the output from the triggered 5 sensors, and may determine (at 3) that the number of simultaneously or contemporaneously triggered sensors is greater than a threshold number specified for a target object (e.g., a baseball). For instance, the threshold number of sensors that should be triggered by the target object may be 2 when the spacing separating 2 adjacent sensors is equal to or greater than the diameter of the moving object. In this example, the 5 adjacent sensors may be triggered in response to a swung baseball bat, an arm, or other object crossing over tracking device 100. Accordingly, processor 160 may detect the false positive and may ignore (at 4) the output rather than determine a position of the object within a user-defined strike zone.

Figure 12:
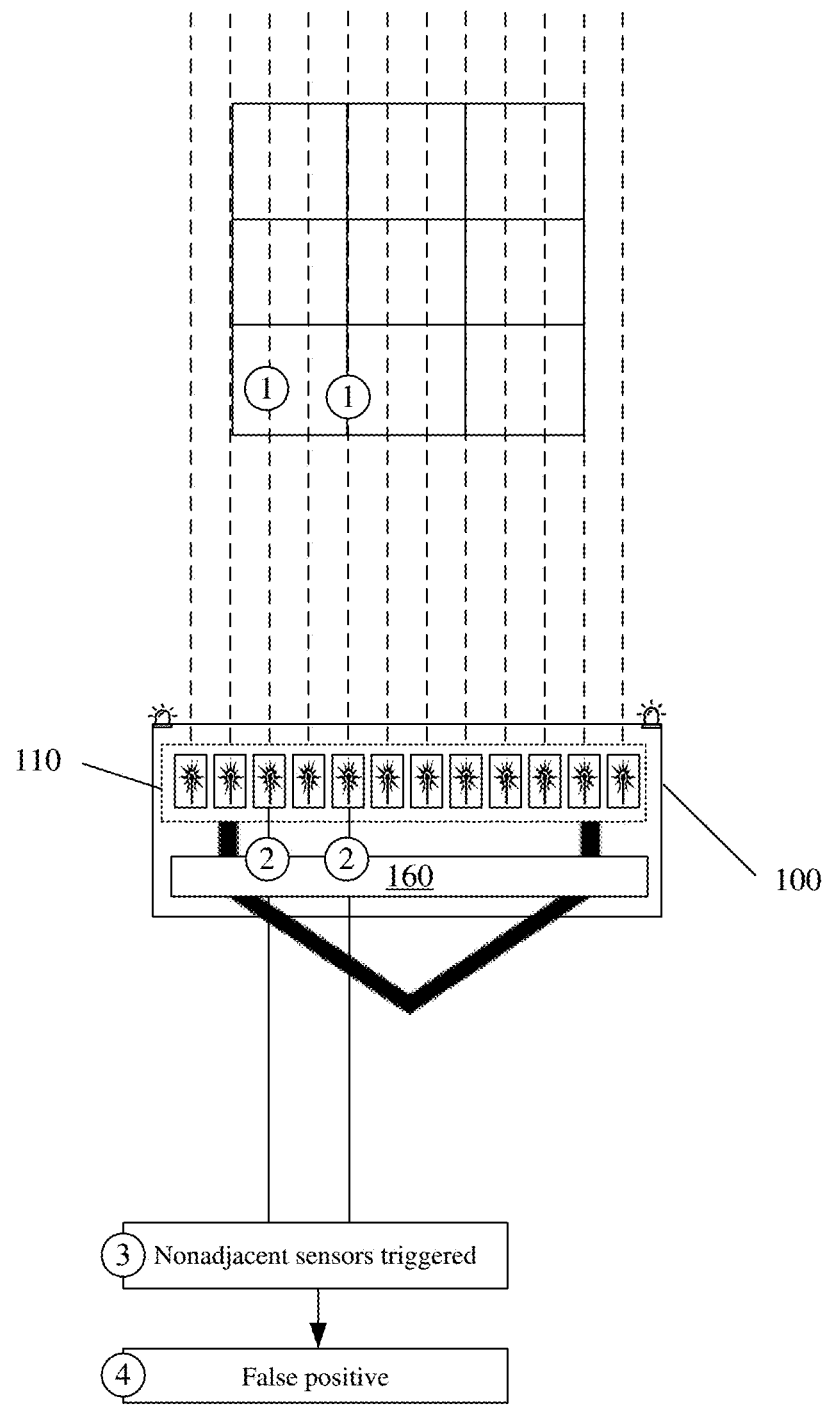
FIG. 12 illustrates an anomaly detection example that is based on the triggering of nonadjacent sensors in accordance with some embodiments presented herein.

FIG. 12 illustrates an example of anomaly detection by tracking device 100 that is based on the triggering of nonadjacent sensors 110 in accordance with some embodiments presented herein. As shown in FIG. 12, a moving object simultaneously or contemporaneously (e.g., within a few millisecond) produces (at 1) similar height measurements on 2 nonadjacent sensors 110.

Processor 160 may receive (at 2) the output from the 2 nonadjacent sensors, and may determine (at 3) from sensor identifiers included with the sensor output that the measurements are for an undesired object because the output is produced by nonadjacent sensors. Specifically, the desired target object has a diameter, width, or shape that would produce output on at least 2 to 3 adjacent sensors depending on its movement. In some embodiments, the output of each sensor 110 is tagged with a sensor identifier that identifies which sensor 100 produces the output, and the identifier can be mapped to a particular sensor location such that nonconsecutive sensor identifiers identify output from nonadjacent sensors. Accordingly, processor 160 may detect the false positive and may ignore (at 4) the output rather than determine a position of the object within a user-defined strike zone.

Figure 13:
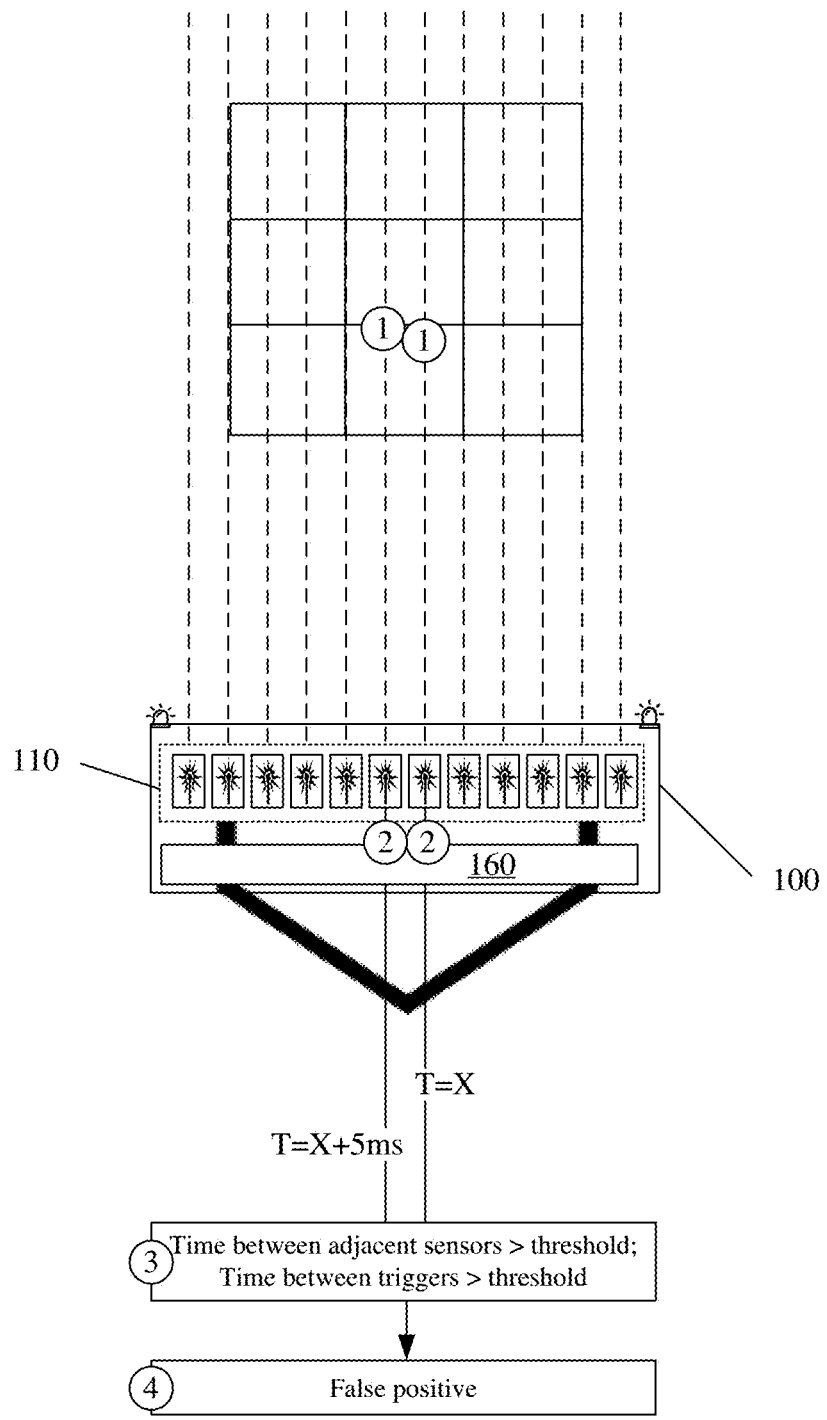
FIG. 13 illustrates an anomaly detection example that is based on the timing of sensor output in accordance with some embodiments presented herein.

FIG. 13 illustrates an example of anomaly detection by tracking device 100 that is based on the timing of sensor output in accordance with some embodiments presented herein. As shown in FIG. 13, a moving object produces (at 1) similar height measurements on 2 adjacent sensors 110. However, the height measurements are produced at times that are separated by more than a specified time threshold.

Processor 160 may receive (at 2) the output from the 2 adjacent sensors, and may determine (at 3) from timestamps associated with measurement output from each of the 2 adjacent sensors, or from when processor 160 receives (at 2) the output from each of the 2 adjacent sensors, that the timing of the measurements is not within the specified time threshold. For instance, the time threshold may require that measurements output from sensors 110 should be within 3 milliseconds ("ms") of one another to be considered part of the same object, and the measurements taken by the 2 adjacent sensors in FIG. 13 differ by 5 ms. Accordingly, processor 160 may determine that the sensor output is produced by two separate objects or an object with a shape that is different from the shape of the desired target object. Accordingly, processor 160 may detect the false positive and may ignore (at 4) the output rather than determine a position of the object within a user-defined strike zone.

Figure 14:
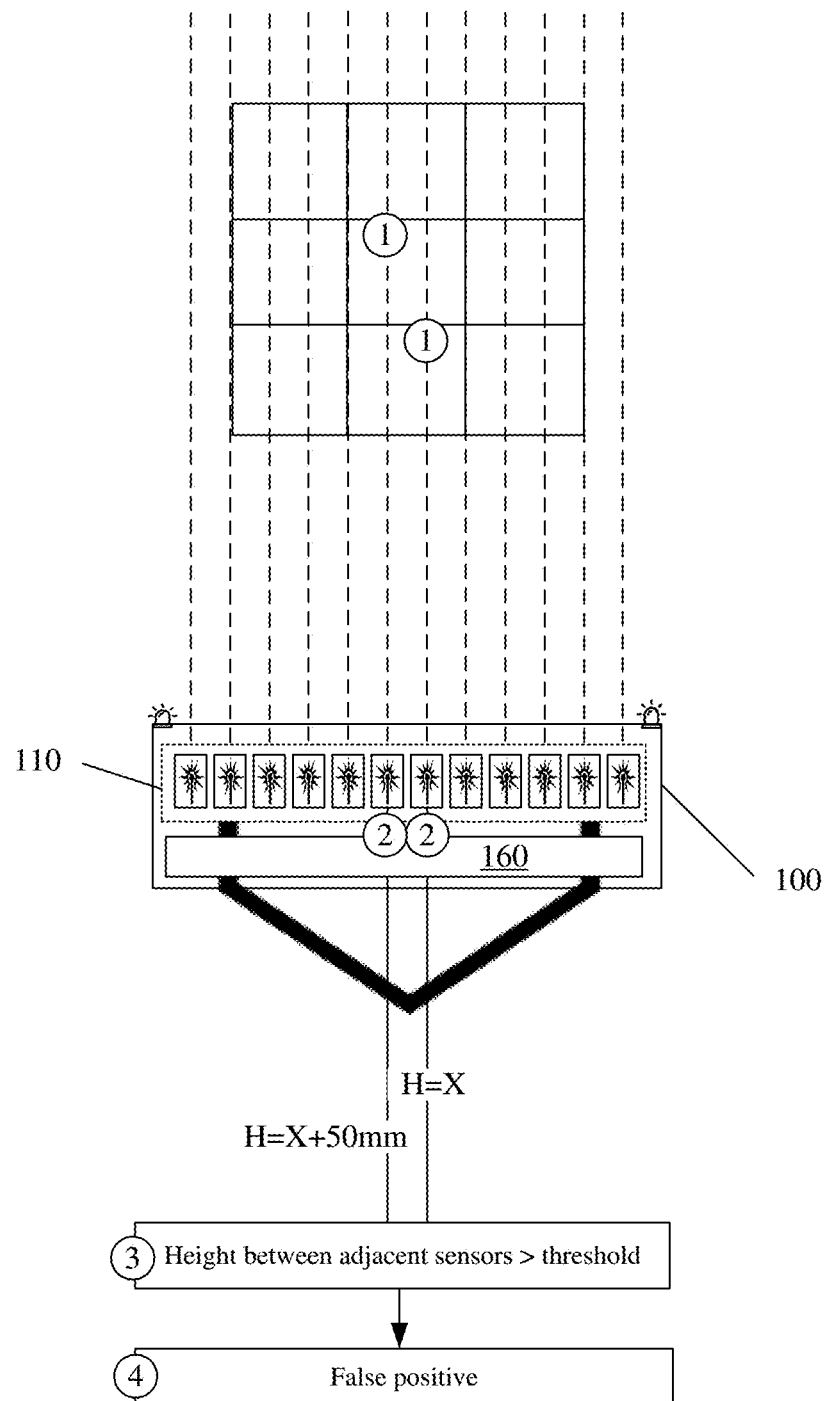
FIG. 14 illustrates an anomaly detection example that is based on the height measurements output from sensors in accordance with some embodiments presented herein.

FIG. 14 illustrates an example of anomaly detection by tracking device 100 that is based on the height measurements output from sensors 110 in accordance with some embodiments presented herein. As shown in FIG. 14, a moving object simultaneously or contemporaneously produces (at 1) height measurements on 2 adjacent sensors 110. However, the height measurements differ by a distance that is greater than a specified distance threshold. The different height measurement may be due to the detection of two separate objects or an undesired object with an irregular shape or shape that is different than that of the desired target object.

Processor 160 may receive (at 2) the output from the 2 adjacent sensors, and may determine (at 3) from the height measurement output from each of the 2 adjacent sensors that the difference between the height measurements is greater than the specified distance threshold. For instance, the distance threshold may require that height measurements output from sensors 110 should be within 20 millimeters ("mm") of one another to be considered part of the same object, and the height measurements taken by the 2 adjacent sensors in FIG. 14 differ by 50 mm. Accordingly, processor 160 may detect the false positive and may ignore (at 4) the output rather than determine a position of the object within a user-defined strike zone.

Figure 15:
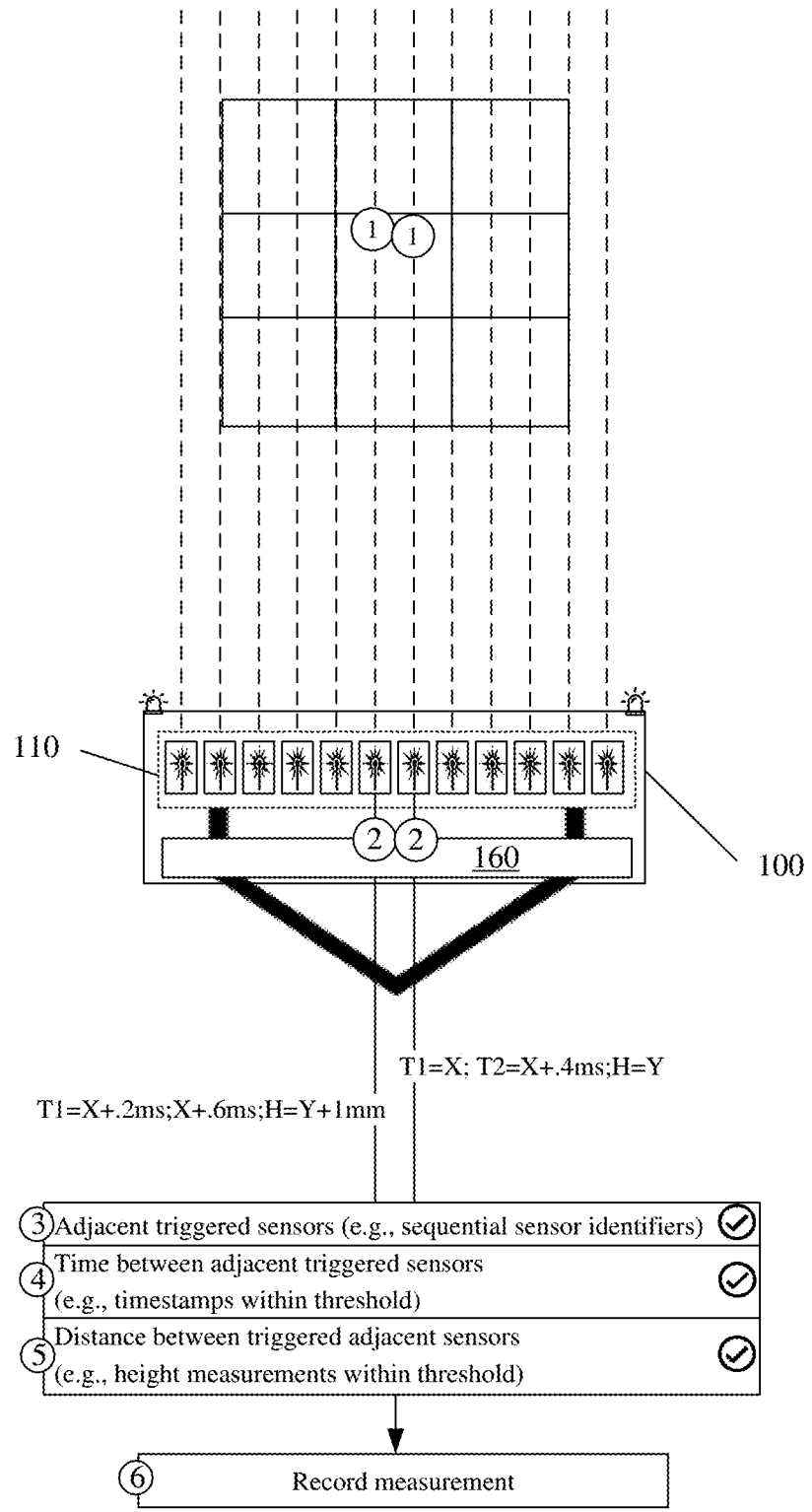
FIG. 15 illustrates an example of a moving object that does not trigger the anomaly detection and produces valid output tracked by the tracking device in accordance with some embodiments presented herein.

FIG. 15 illustrates an example of a moving object that does not trigger the anomaly detection and produces valid output tracked by tracking device 100 in accordance with some embodiments presented herein. As shown in FIG. 15, a moving object simultaneously or contemporaneously produces (at 1) height measurements on 2 adjacent sensors 110.

Processor 160 may receive (at 2) the output from the 2 adjacent sensors. Processor 160 may perform a series of anomaly checks against the received (at 2) output. For instance, processor 160 may compare (at 3) identifiers that identify which sensors 110 produced the output in order to verify that the output comes from adjacent sensors. Processor 160 may compare (at 4) timestamps or times when the output is received (at 2) from each sensor in order to verify that the output is produced simultaneously and/or contemporaneously (e.g., within 3 ms) which is one indicia that the output is produced by the same object. Processor 160 may compare (at 5) the height measurements in the received output in order to verify that the measured distances indicate the same object creating the measurements.

In response to successfully completing each of the checks, processor 160 may determine that the measurements are valid and for the desired target object. Accordingly, processor 160 may record (at 6) the measurements and/or derive results from the received (at 2) output.

In some embodiments, tracking device 100 may improve accuracy of a tracked object by recording a location for the object that is derived from a center point of the subset of sensors 110 producing the output used to detect the object. For instance, in FIG. 15, tracking device 100 may identify the horizontal position of the pitch to have a coordinate or value that is in between the horizontal coordinates or values of the 2 adjacent sensors used to detect the pitch. Similarly, tracking device 100 may identify the vertical position of the pitch to have a coordinate or value that is in between the vertical coordinates or values identified in the height measurements output from the 2 adjacent sensors. Thus if the first detecting sensor in FIG. 15 output a measurement of (x1,y1) and the adjacent second detecting sensor in FIG. 15 output a measurement of (x2,y2), processor 160 may compute a location of ((x1+x2)/2,(y1+y2)/2) for the detected pitch. When an odd number (e.g., 3) of sensors 110 are used to detect an object, then tracking device 100 may set the horizontal position of the object to coincide with the position of the middle detecting sensor, and may set the vertical position of the object to be the centermost height measurement or an average of the height measurements.

In some embodiments, tracking device 100 may improve training, practice, and/or gameplay by using network connectivity 140 to integrate with other third-party devices. In particular, tracking device 100 may incorporate input from one or more third-party devices with the results produced by tracking device 100 from the verified and validated output of sensors 110. For instance, an umpire, coach, pitcher, or other user may input their classification of a pitch on a third-party device, and the input from the third-party device may be compared against output produced by tracking device 100 for the same pitch to determine the accuracy of the classification made by the user. In some embodiments, tracking device 100 may improve training, practice, and/or gameplay by directly incorporating input from a user via microphone 130 or other component of tracking device 100 without the need for incorporating the input from a third-party device used by the user.

Figure 16:
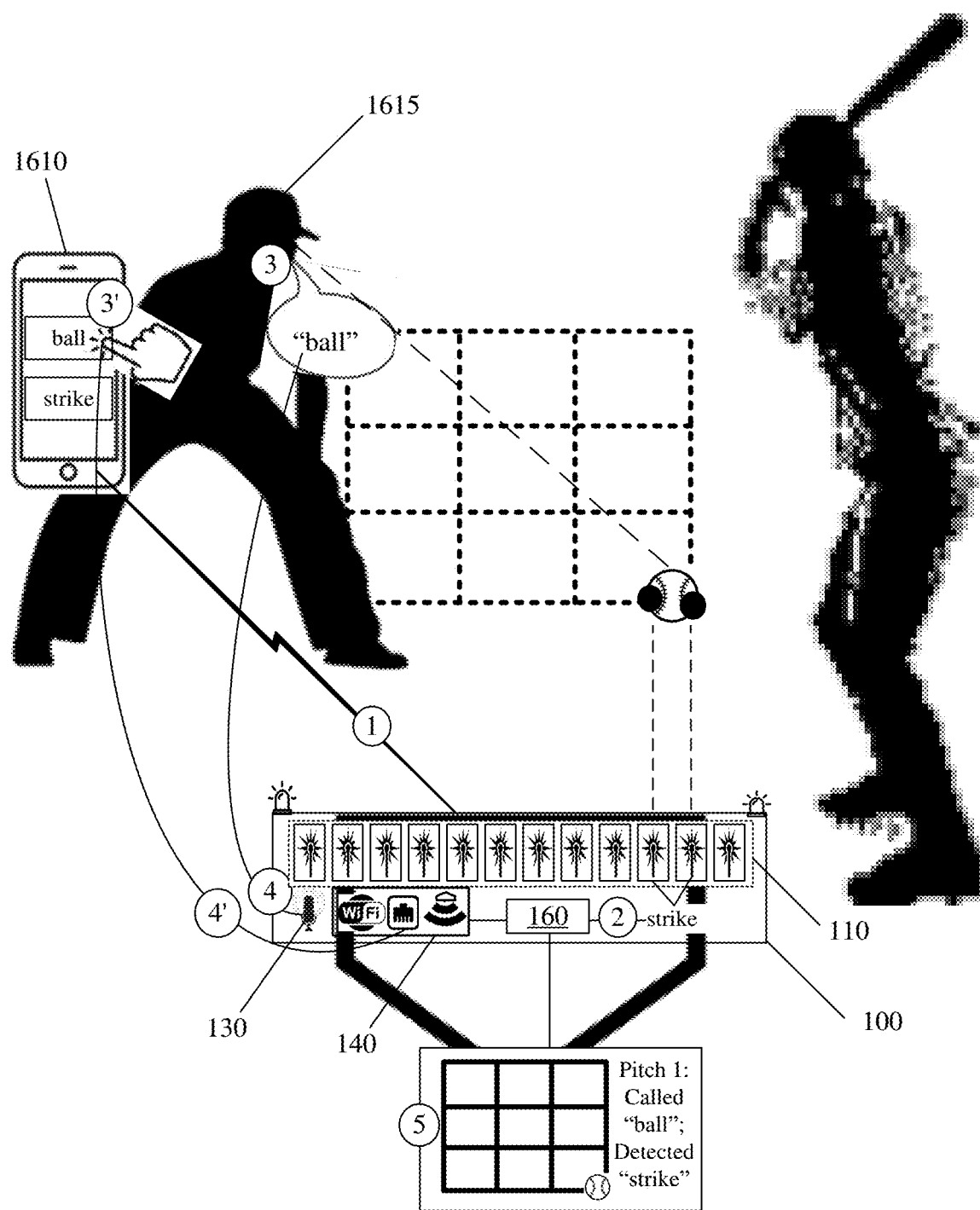
FIG. 16 illustrates an example of incorporating input from a third-party device or user with output of the tracking device in accordance with some embodiments presented herein.

FIG. 16 illustrates an example of incorporating input from third-party device 1610 or user 1615 with output of tracking device 100 in accordance with some embodiments presented herein. A network connection may be established (at 1) between third-party device 1610 of user 1615 and tracking device 100. However, the network connection may be optional when incorporating input directly from user 1615 using microphone 130 of tracking device 100.

Sensors 110 of tracking device 100 may detect a moving object. In response to detecting the moving object, sensors 110 may produce output with measurements and/or other data for when the moving object crossed over tracking device 100.

Based on the sensor output and a configured user-defined strike zone, tracking device 100, by operation of processor 160, may determine (at 2) that the moving object is a pitch that falls within the bottom right corner of the user-defined strike zone. Accordingly, processor 160 may classify the pitch as a strike and may store location information for that pitch relative to the user-defined strike zone.

Tracking device 100 may receive (at 4 or 4') input from user 1615. In some embodiments, the input may be obtained (at 4) using microphone 130 to record an audible "ball" call spoken (at 3) by user 1615. In some such embodiments, tracking device 100 may operate without establishing the network connection to user device 1610. In some other embodiments, the input may be obtained (at 4') via wireless messaging that is passed from user device 1610 to tracking device 100 via network connectivity 140 and/or the network connection established with user device 1610. For instance, user 1615 may access an application running on user device 1610, and may provide (at 3') input to the application that classifies the pitch as a ball or a strike by pressing one of two buttons. Additionally, user 1615 may provide input that identifies a position of the pitch in the strike zone as observed by user 1615.

Tracking device 100, by operation of processor 160, may compare the received (at 4 or 4') input against the result determined from the sensor output to further determine if the input from user 1615 is accurate or inaccurate. In the example illustrated by FIG. 16, user 1615 issues a "ball" call for the observed pitch while tracking device 100 determines that the pitch falls within the user-defined strike zone and is therefore a strike. Accordingly, tracking device 100, by operation of processor 160, may track (at 5) the user's call as a missed or inaccurate call. Tracking device 100 may further track (at 5) the detected location of the pitch in the user-defined strike zone with the inaccurate call of user 1615 to provide visual feedback for training, game, or other purposes. The results may be tracked to memory or storage 150 with results from other pitches. The tracked results can be subsequently accessed by user 1615 or another user to determine accuracy and/or to train the user. In some embodiments, a summarized view of all calls and tracked results may be presented with or without each call and the corresponding tracked result being presented individually. In some embodiments, each call and the corresponding tracked result is transmitted from tracking device 100 to user device 1610 in real-time as each call and tracked result is produced.

Figure 17:
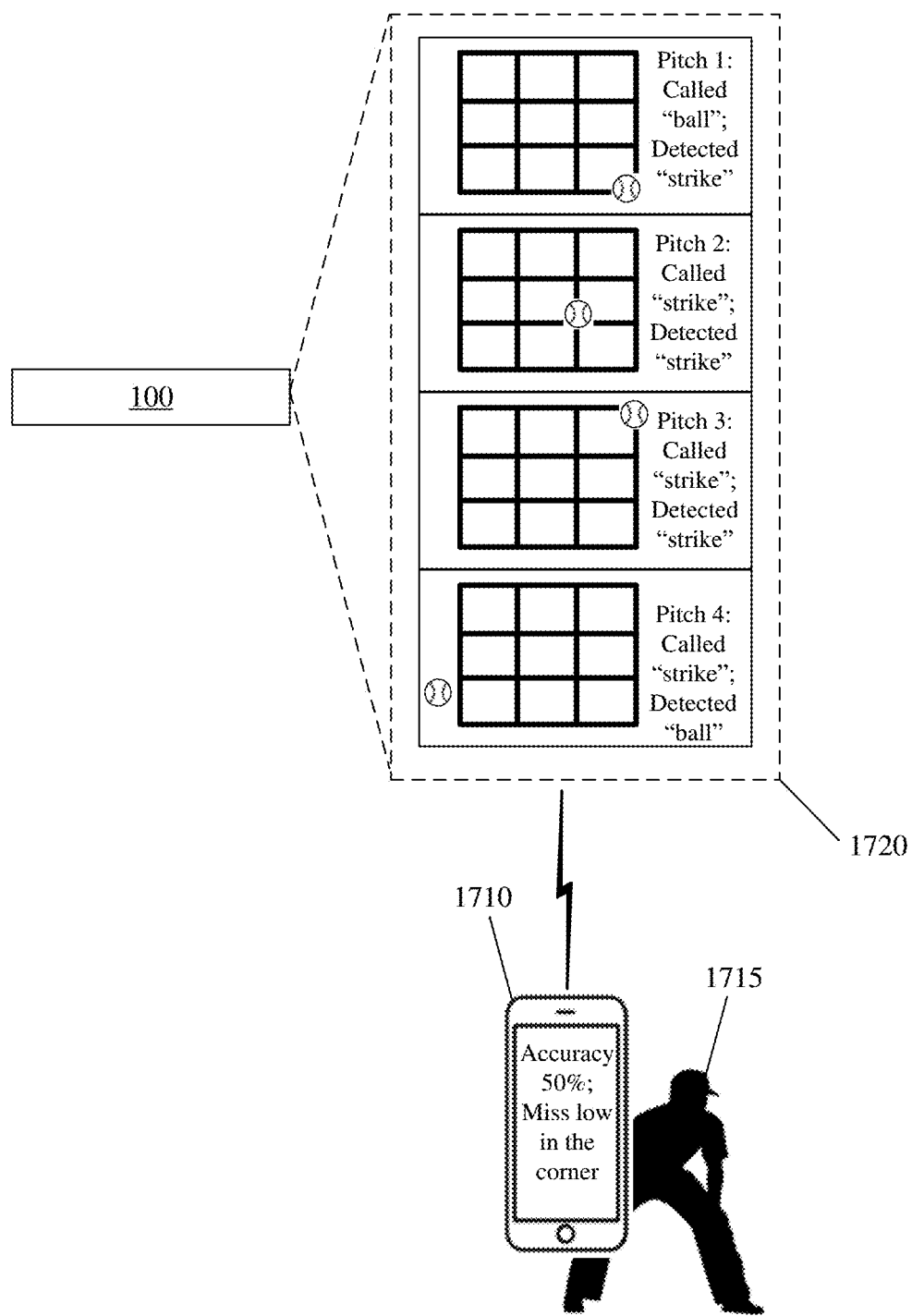
FIG. 17 illustrates a user device accessing a sequence of results produced by the tracking device in accordance with some embodiments presented herein.

FIG. 17 illustrates user device 1710 accessing a sequence of results 1720 produced by tracking device 100 in accordance with some embodiments presented herein. As shown in FIG. 17, tracking device 100 may track results 1720 of a pitch sequence that incorporates input from user 1715. Specifically, results 1720 identify a location of each pitch in the pitch sequence about a user-defined strike zone based on measurements obtained from sensors 110. Results 1720 may also identify the input from user 1715 that classifies each pitch in the pitch sequence as a ball or a strike.

A result summary may be generated on user device 1710 to identify the overall accuracy of the user input for identifying the pitches of the pitch sequence, and/or to provide additional feedback. For instance, the additional feedback may include using patterns, artificial intelligence, and/or machine learning to identify specific issues (e.g., missed calls for low pitches in the corners) that resulted in user input inaccuracies.

In some embodiments, results 1720 may be presented in a graphical user interface. The graphical user interface may present the user-defined strike zone with the detected location of each pitch in the pitch sequence along with the user's call for each pitch. In some embodiments, results 1720 may be presented as textual data, statistical data, or raw data.

In some embodiments, the comparison of the call to the detected result may be performed on user device 1610 instead of tracking device 100. In some such embodiments, tracking device 100 may submit the pitch result, that is determined from the sensor output, and/or the detected location of the pitch in the user-defined strike zone to user device 1610. User device 1610 may then compare the user-provided input to the output from tracking device 100.

Tracking device 100 may implement methods that create training games. For instance, in addition to tracking the location of a pitch, tracking device 100 may first notify a pitcher on where to locate the pitch, and may then determine if the pitcher successfully executed the pitch by hitting the identified pitch location.

In some embodiments, tracking device 100 may be programmed with a pitch plan. For instance, a connected user device may provide the pitch plan to tracking device 100 via a set of messages. The pitch plan may include a sequence of pitches for hitting different locations in one or more user-defined strike zones, and/or may further include instructions for throwing different types of pitches (e.g., fastball, breaking ball, slider, changeup, etc.) at the different locations. Tracking device 100 may then track the accuracy of the pitcher in replicating pitches from the pitch plan, and may produce individual pitch results and/or a summarized result for the pitch plan.

Figure 18:
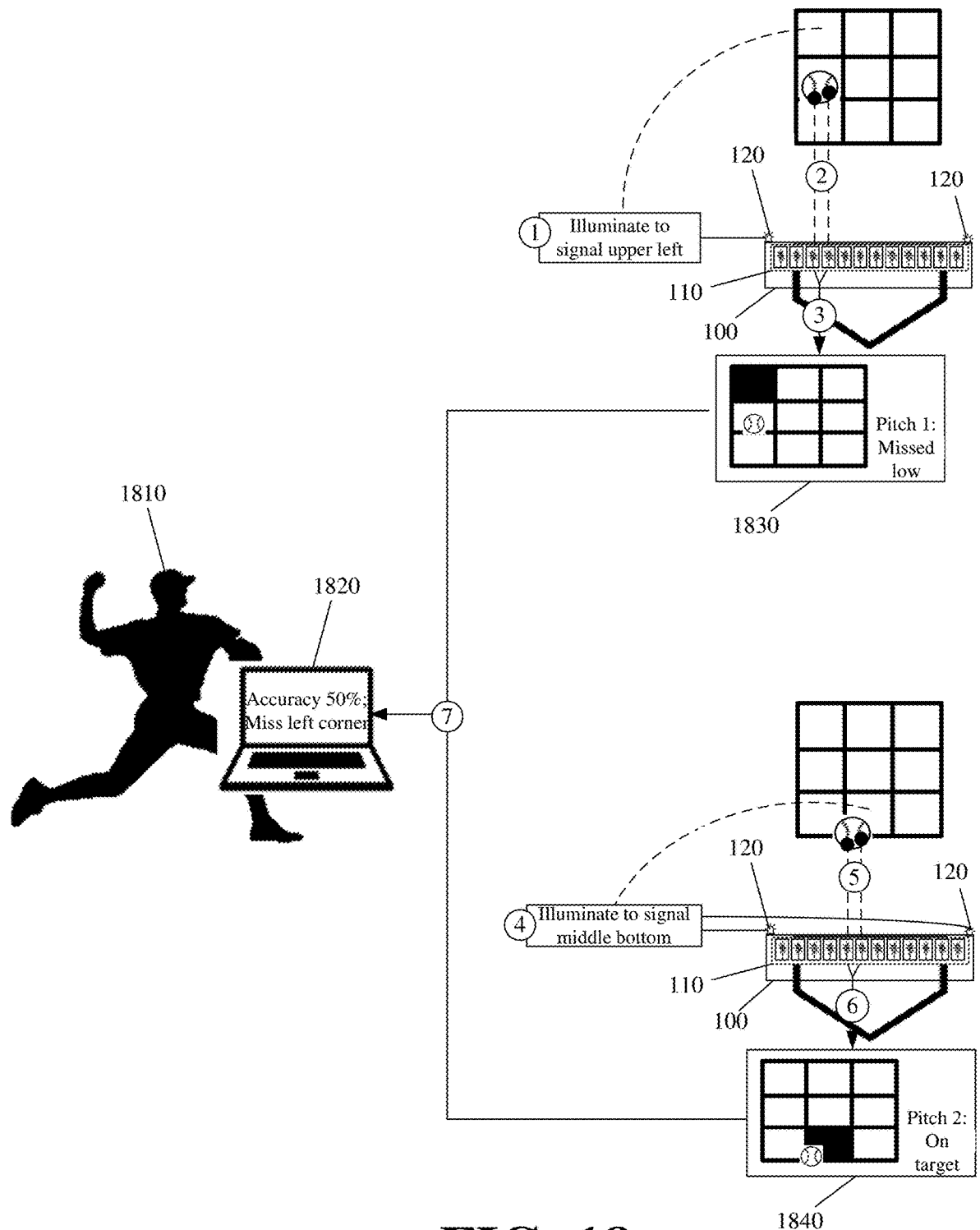
FIG. 18 illustrates an example of the tracking device executing a training game method and tracking the user results for the game in accordance with some embodiments presented herein.

FIG. 18 illustrates an example of tracking device 100 executing a training game method and tracking the user results for the game in accordance with some embodiments presented herein. Executing the training game method may include illuminating (at 1) one or more visual indicators 120 of tracking device 100 to instruct pitcher 1810 on a first desired pitch location, a type of pitch to throw, and/or other instruction. The first desired pitch location may identify the upper left quadrant of the strike zone. In some embodiments, the instruction notifying pitcher 1810 of the first desired pitch location may be wirelessly transmitted to user device 1820 of pitcher 1810, a coach, or other user that can relay the instruction to pitcher 1810.

In response to the notification of the first desired pitch location, pitcher 1810 may throw a first pitch attempting to locate the pitch in the first desired pitch location. Tracking device 100 detects (at 3) the actual location of the first pitch based on measurements and/or output obtained (at 2) from sensors 110. As shown in FIG. 18, tracking device 100 detects (at 3) the actual location of the first pitch to fall within the middle left quadrant which misses the first desired pitch location of the upper left quadrant. Accordingly, tracking device 100 may record first pitch result 1830 in memory or storage 150. First pitch result 1830 may include an indication that the first desired pitch location was missed or was not successfully executed. First pitch result 1830 may include data that identifies the actual pitch location and the first desired pitch location in the strike zone.

In response to detecting that the first pitch was thrown or recording first pitch result 1830, tracking device 100 may advance through the configured pitch plan by illuminating (at 4) one or more visual indicators 120 of tracking device 100 to instruct pitcher 1810 on a different second desired pitch location, a second type of pitch to throw, and/or other instruction. The second desired pitch location may identify the bottom middle quadrant of the strike zone.

In response to the notification of the second desired pitch location, pitcher 1810 may throw a second pitch, and may attempt to locate the second pitch in the second desired pitch location. Tracking device 100 detects (at 6) the actual location of the second pitch based on measurements and/or output obtained (at 5) from sensors 110. As shown in FIG. 18, tracking device 100 detects (at 6) the actual location of the second pitch to intersect the middle bottom quadrant which hits or matches the second desired pitch location of the bottom middle quadrant. Accordingly, tracking device 100 may record second pitch result 1840 in memory or storage 150 to include an indication that the second desired pitch location was successfully executed and/or to include data that identifies the actual location of the second pitch and the second desired pitch location in the strike zone.

In some embodiments, first pitch result 1830 may be transmitted to user device 1820 after result 1830 is generated, and second pitch result 1840 may be transmitted to user device 1820 after result 1840 is generated. In some other embodiments, tracking device 100 may provide (at 7) first pitch result 1830 and second pitch result 1840, other pitch results, and/or a summarized presentation of the pitch results to user device 1820 at the end of a pitch sequence.

Figure 19:
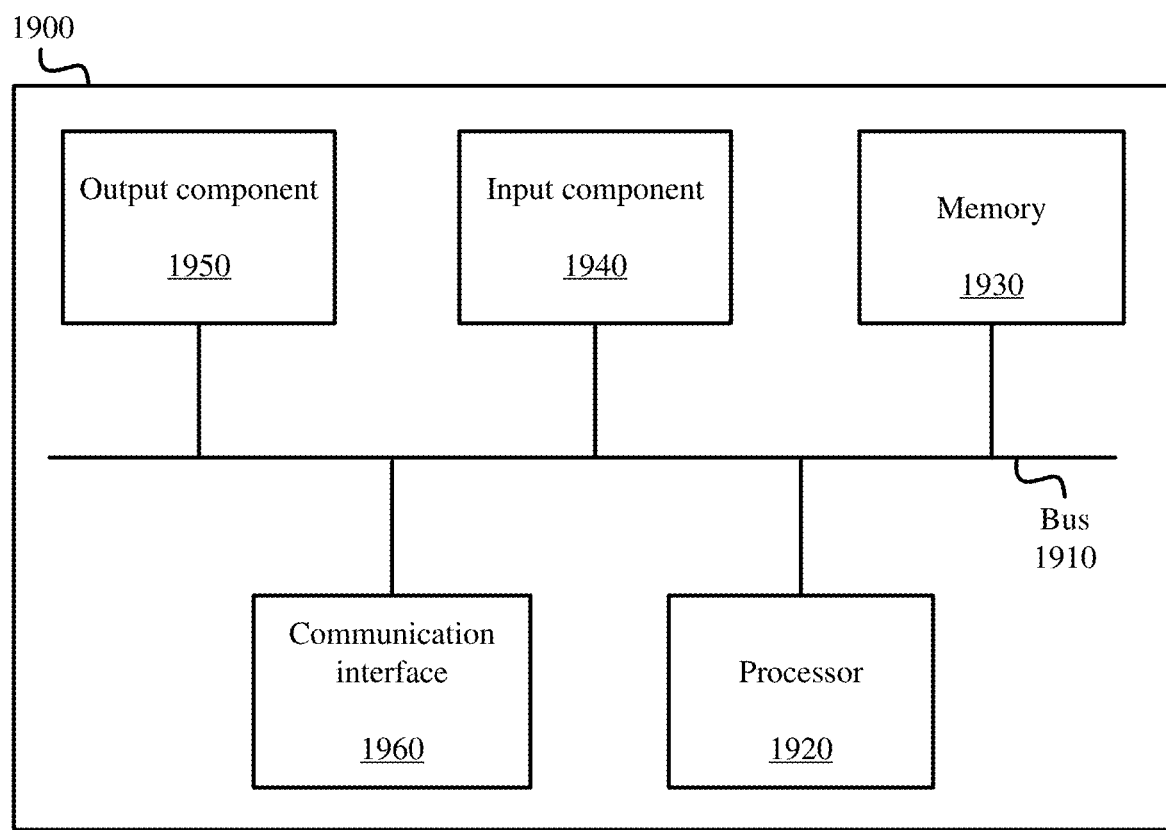
FIG. 19 illustrates example components of one or more devices, according to one or more embodiments described herein.

FIG. 19 is a diagram of example components of device 1900. Device 1900 may be used to implement one or more of the devices or systems described above (e.g., tracking device 100, user devices, etc.). Device 1900 may include bus 1910, processor 1920, memory 1930, input component 1940, output component 1950, and communication interface 1960. In another implementation, device 1900 may include additional, fewer, different, or differently arranged components.

Bus 1910 may include one or more communication paths that permit communication among the components of device 1900. Processor 1920 may include a processor, microprocessor, or processing logic that may interpret and execute instructions. Memory 1930 may include any type of dynamic storage device that may store information and instructions for execution by processor 1920, and/or any type of non-volatile storage device that may store information for use by processor 1920.

Input component 1940 may include a mechanism that permits an operator to input information to device 1900, such as a keyboard, a keypad, a button, a switch, etc. Output component 1950 may include a mechanism that outputs information to the operator, such as a display, a speaker, one or more light emitting diodes ("LEDs"), etc.

Communication interface 1960 may include any transceiver-like mechanism that enables device 1900 to communicate with other devices and/or systems. For example, communication interface 1960 may include an Ethernet interface, an optical interface, a coaxial interface, or the like. Communication interface 1960 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 1900 may include more than one communication interface 1960. For instance, device 1900 may include an optical interface and an Ethernet interface.

Device 1900 may perform certain operations relating to one or more processes described above. Device 1900 may perform these operations in response to processor 1920 executing software instructions stored in a computer-readable medium, such as memory 1930. A computer-readable medium may be defined as a non-transitory memory device. A memory device may include space within a single physical memory device or spread across multiple physical memory devices. The software instructions may be read into memory 1930 from another computer-readable medium or from another device. The software instructions stored in memory 1930 may cause processor 1920 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations. For instance, the devices may be arranged according to different peer-to-peer, private, permissioned, and/or other blockchain networks.

The actual software code or specialized control hardware used to implement an embodiment is not limiting of the embodiment. Thus, the operation and behavior of the embodiment has been described without reference to the specific software code, it being understood that software and control hardware may be designed based on the description herein.

For example, while series of messages, blocks, and/or signals have been described with regard to some of the above figures, the order of the messages, blocks, and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Some implementations described herein may be described in conjunction with thresholds. The term "greater than" (or similar terms), as used herein to describe a relationship of a value to a threshold, may be used interchangeably with the term "greater than or equal to" (or similar terms). Similarly, the term less than (or similar terms), as used herein to describe a relationship of a value to a threshold, may be used interchangeably with the term "less than or equal to" (or similar terms). As used herein, "exceeding" threshold (or similar terms) may be used interchangeably with "being greater than a threshold," "being greater than equal to a threshold," "being less than a threshold," "being less than or equal to a threshold," or other similar terms, depending on the context in which the threshold is used.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:

1. A method comprising:
    activating a set of sensors that are positioned adjacent to one another in a row;
    detecting movement of an object over a subset of the set of sensors in response to each particular sensor of the subset of sensors generating output with a timestamp corresponding to a time at which the particular sensor generates the output, and a value corresponding to a height measurement by the particular sensor;
    discarding the output from the subset of sensors in response to the output from the subset of sensors deviating from a set of thresholds, wherein discarding the output comprises at least one of:
        determining that the output from the subset of sensors violates a positioning threshold of the set of thresholds based on the output being generated by at least one sensor that is separated from a next sensor in the subset of sensors by at least two or more sensors of the set of sensors,
        determining that the output from the subset of sensors violates a size threshold of the set of thresholds based on the output generated by the subset of sensors comprising output that is generated by a first number of the set of sensors that is greater than a high number of sensors set as the size threshold, or that is less than a low number of sensors set as the size threshold, or
        determining that a first height measurement generated by a first sensor of the subset of sensors differs by more than a distance threshold from a second height measurement generated by a second sensor of the subset of sensors; and
    tracking a vertical position and a horizontal position of the object in response to the output from the subset of sensors satisfying the set of thresholds, and further in response to a positioning of the subset of sensors in the row and the height measurement generated by each sensor of the subset of sensors.

2. The method of claim 1, wherein discarding the output further comprises:
    determining that a first timestamp generated by a first sensor of the subset of sensors is different by more than a time threshold from a second timestamp generated by a second sensor of the subset of sensors.

3. The method of claim 1, wherein said tracking comprises:
    verifying that the object has a shape and size of a target object based on the subset of sensors equaling a threshold number of sensors, the timestamp generated by each of the subset of sensors falling within a time threshold of one another, and the height measurement generated by each of the subset of sensors being within a distance threshold of one another.

4. The method of claim 1 further comprising:
    differentiating between a ball that is thrown and a bat that is swung based on one or more of a number and position of the subset of sensors from the set of sensors, the timestamp generated by each of the subset of sensors, and the height measurement by each of the subset of sensors.

5. The method of claim 4 further comprising:
    detecting the object to be a bat that is swung in response to the output from the subset of sensors deviating from the set of thresholds; and
    detecting the object to be a ball that is thrown in response to the output from the subset of sensors satisfying the set of thresholds.

6. The method of claim 1 further comprising:
    deactivating a set of visual indicators of a device with the set of sensors in response to said discarding; and
    activating one or more of the set of visual indicators in response to said tracking.

7. The method of claim 6, wherein said activating comprises:
    illuminating a first subset of the set of visual indicators in response to tracking the vertical position and the horizontal position of the object to be within a defined strike zone; and
    illuminating a different second subset of the set of visual indicators in response to tracking the vertical position and the horizontal position of the object to be outside the defined strike zone.

8. The method of claim 1 further comprising:
    providing a first classification for the object in response to tracking the vertical position and the horizontal position of the object to be within a defined area; and
    providing a different second classification for the object in response to tracking the vertical position and the horizontal position of the object to be outside the defined area.

9. The method of claim 1 further comprising:
reproducing a sequence of pitches thrown by a pitcher based on tracking a corresponding sequence of the vertical position and the horizontal position of the object over a duration.

10. The method of claim 1 further comprising:
illuminating one or more of a set of visual indicators of a device with the set of sensors, wherein said illuminating indicates a desired vertical position and a desired horizontal position at which the object is to cross over the set of sensors;
generating first output in response to tracking the vertical position and the horizontal position of the object to be within a threshold range of the desired vertical position and the desired horizontal position; and
generating second output in response to tracking the vertical position and the horizontal position of the object to be outside the threshold range of the desired vertical position and the desired horizontal position.

11. The method of claim 1 further comprising:
tagging the output from each sensor of the subset of sensors with a different sensor identifier, wherein the sensor identifier identifies a position of a sensor within the set of sensors; and
wherein discarding the output further comprises determining that the subset of sensors includes nonadjacent sensors of the set of sensors based on the sensor identifier tagged with the output.

12. The method of claim 1 further comprising:
mapping the vertical position and the horizontal position of the object to a defined zone; and
providing different classifications based on said mapping.

13. The method of claim 1, wherein said tracking comprises:
defining the horizontal position to correspond to a position of a middle sensor of the subset of sensors when the subset of sensors comprises an odd number of sensors.

14. The method of claim 13, wherein said tracking further comprises:
defining the horizontal position to correspond to a position between two central sensors of the subset of sensors when the subset of sensors comprises an even number of sensors.

15. The method of claim 1 further comprising:
defining a plurality of quadrants distributed across multiple rows within a zone defined by a first height and a second height; and
wherein said tracking comprises identifying a location of the object in one or more of the plurality of quadrants based on a mapping of the vertical position and the horizontal position of the object to a position of the one or more quadrants.

16. The method of claim 1, wherein said tracking comprises:
presenting a graphical user interface displaying a zone within an area tracked by the set of sensors, and the vertical position and the horizontal position of the object in the zone.

17. A device comprising:
a set of sensors that are positioned adjacent to one another in a row; and
one or more processors configured to:
detect movement of an object over a subset of the set of sensors in response to each particular sensor of the subset of sensors generating output with a timestamp corresponding to a time at which the particular sensor generates the output, and a value corresponding to a height measurement by the particular sensor;
discard the output from the subset of sensors in response to the output from the subset of sensors deviating from a set of thresholds, wherein discarding the output comprises at least one of:
determining that the output from the subset of sensors violates a positioning threshold of the set of thresholds based on the output being generated by at least one sensor that is separated from a next sensor in the subset of sensors by at least two or more sensors of the set of sensors,
determining that the output from the subset of sensors violates a size threshold of the set of thresholds based on the output generated by the subset of sensors comprising output that is generated by a first number of the set of sensors that is greater than a high number of sensors set as the size threshold, or that is less than a low number of sensors set as the size threshold, or
determining that a first height measurement generated by a first sensor of the subset of sensors differs by more than a distance threshold from a second height measurement generated by a second sensor of the subset of sensors; and
track a vertical position and a horizontal position of the object in response to the output from the subset of sensors satisfying the set of thresholds, and further in response to a positioning of the subset of sensors in the row and the height measurement generated by each sensor of the subset of sensors.

18. A method comprising:
activating a set of sensors that are positioned adjacent to one another in a row;
detecting movement of an object over a subset of the set of sensors in response to each particular sensor of the subset of sensors generating output with a timestamp corresponding to a time at which the particular sensor generates the output, and a value corresponding to a height measurement by the particular sensor;
discarding the output from the subset of sensors in response to the output from the subset of sensors deviating from a set of thresholds;
deactivating a set of visual indicators of a device with the set of sensors in response to said discarding; and
tracking a vertical position and a horizontal position of the object in response to the output from the subset of sensors satisfying the set of thresholds, and further in response to a positioning of the subset of sensors in the row and the height measurement generated by each sensor of the subset of sensors; and
activating one or more of the set of visual indicators in response to said tracking.

19. A device comprising:
a set of sensors that are positioned adjacent to one another in a row;
a set of visual indicators; and
one or more processors configured to:
detect movement of an object over a subset of the set of sensors in response to each particular sensor of the subset of sensors generating output with a timestamp corresponding to a time at which the particular sensor generates the output, and a value corresponding to a height measurement by the particular sensor;
discard the output from the subset of sensors in response to the output from the subset of sensors deviating from a set of thresholds;

deactivate the set of visual indicators in response to said discarding;

track a vertical position and a horizontal position of the object in response to the output from the subset of sensors satisfying the set of thresholds, and further in response to a positioning of the subset of sensors in the row and the height measurement generated by each sensor of the subset of sensors; and activate one or more of the set of visual indicators in response to said tracking.

20. A method comprising:

illuminating one or more of a set of visual indicators to indicate a desired vertical position and a desired horizontal position at which an object is to cross over a set of sensors that are positioned adjacent to one another in a row;

activating the set of sensors;

detecting movement of the object over a subset of the set of sensors in response to each particular sensor of the subset of sensors generating output with a timestamp corresponding to a time at which the particular sensor generates the output, and a value corresponding to a height measurement by the particular sensor;

tracking a vertical position and a horizontal position of the object in response to the output from the subset of sensors satisfying a set of thresholds, and further in response to a positioning of the subset of sensors in the row and the height measurement generated by each sensor of the subset of sensors;

generating first output in response to tracking the vertical position and the horizontal position of the object to be within a threshold range of the desired vertical position and the desired horizontal position; and generating second output in response to tracking the vertical position and the horizontal position of the object to be outside the threshold range of the desired vertical position and the desired horizontal position.

21. A device comprising:

a set of sensors that are positioned adjacent to one another in a row;

a set of visual indicators; and one or more processors configured to:
  illuminate one or more of the set of visual indicators to indicate a desired vertical position and a desired horizontal position at which an object is to cross over the set of sensors;
  detect movement of the object over a subset of the set of sensors in response to each particular sensor of the subset of sensors generating output with a timestamp corresponding to a time at which the particular sensor generates the output, and a value corresponding to a height measurement by the particular sensor;
  track a vertical position and a horizontal position of the object in response to the output from the subset of sensors satisfying a set of thresholds, and further in response to a positioning of the subset of sensors in the row and the height measurement generated by each sensor of the subset of sensors;
  generate first output in response to tracking the vertical position and the horizontal position of the object to be within a threshold range of the desired vertical position and the desired horizontal position; and
  generate second output in response to tracking the vertical position and the horizontal position of the object to be outside the threshold range of the desired vertical position and the desired horizontal position.

22. A method comprising:

activating a set of sensors that are positioned adjacent to one another in a row;

detecting movement of an object over a subset of the set of sensors in response to each particular sensor of the subset of sensors generating output with a timestamp corresponding to a time at which the particular sensor generates the output, and a value corresponding to a height measurement by the particular sensor;

discarding the output from the subset of sensors in response to the output from the subset of sensors deviating from a set of thresholds; and tracking a vertical position and a horizontal position of the object in response to the output from the subset of sensors satisfying the set of thresholds, and further in response to a positioning of the subset of sensors in the row and the height measurement generated by each sensor of the subset of sensors, wherein said tracking comprises defining the horizontal position to correspond to a position of a middle sensor of the subset of sensors when the subset of sensors comprises an odd number of sensors.

23. A device comprising:

a set of sensors that are positioned adjacent to one another in a row; and one or more processors configured to:
  detect movement of the object over a subset of the set of sensors in response to each particular sensor of the subset of sensors generating output with a timestamp corresponding to a time at which the particular sensor generates the output, and a value corresponding to a height measurement by the particular sensor;
  discard the output from the subset of sensors in response to the output from the subset of sensors deviating from a set of thresholds; and
  track a vertical position and a horizontal position of the object in response to the output from the subset of sensors satisfying the set of thresholds, and further in response to a positioning of the subset of sensors in the row and the height measurement generated by each sensor of the subset of sensors, wherein said tracking comprises defining the horizontal position to correspond to a position of a middle sensor of the subset of sensors when the subset of sensors comprises an odd number of sensors.

\* \* \* \* \*